US009808633B2

(12) United States Patent
Bonner et al.

(10) Patent No.: US 9,808,633 B2
(45) Date of Patent: Nov. 7, 2017

(54) LEADLESS PACEMAKER SYSTEM

(71) Applicant: Medtronic, Inc., Minneapolis, MN (US)

(72) Inventors: Matthew D. Bonner, Plymouth, MN (US); Saul E. Greenhut, Aurora, CO (US); Todd J. Sheldon, North Oaks, MN (US); Wade M. Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/665,601

(22) Filed: Oct. 31, 2012

(65) Prior Publication Data
US 2014/0121720 A1 May 1, 2014

(51) Int. Cl.
*A61N 1/365* (2006.01)
*A61N 1/375* (2006.01)
*A61N 1/368* (2006.01)
*A61N 1/05* (2006.01)

(52) U.S. Cl.
CPC ......... *A61N 1/3756* (2013.01); *A61N 1/0587* (2013.01); *A61N 1/368* (2013.01); *A61N 1/375* (2013.01); *A61N 1/36507* (2013.01); *A61N 1/36578* (2013.01)

(58) Field of Classification Search
CPC .... A61N 1/0587; A61N 1/368; A61N 1/3702; A61N 1/372; A61N 1/375; A61N 1/3756
USPC ............................................ 607/2, 9, 33, 36
See application file for complete search history.

(56) References Cited

U.S. PATENT DOCUMENTS

| 5,411,535 | A | * | 5/1995 | Fujii et al. ...................... 607/32 |
| 5,683,426 | A | * | 11/1997 | Greenhut et al. ................. 607/9 |
| 5,928,271 | A | | 7/1999 | Hess et al. |
| 6,115,632 | A | * | 9/2000 | Akers .................. A61N 1/3622 607/17 |
| 6,330,477 | B1 | | 12/2001 | Casavant |
| 6,526,311 | B2 | | 2/2003 | Begemann |

(Continued)

FOREIGN PATENT DOCUMENTS

EP  2 471 452 A1  7/2012

OTHER PUBLICATIONS

Hayes et al., "Pacemaker Timing Cycles," Chapter 6 of Cardiac Pacing, edited by Kenneth A. Ellenbogen, M.D., by Blackwell Science, pp. 265-321, 1992 published.

(Continued)

*Primary Examiner* — Michael Carey
*Assistant Examiner* — Pamela M Bays

(57) ABSTRACT

A device includes a signal generator module, a processing module, and a housing. The signal generator module is configured to deliver pacing pulses to an atrium. The processing module is configured to detect a ventricular activation event and determine a length of an interval between the ventricular activation event and a previous atrial event that preceded the ventricular activation event. The processing module is further configured to schedule a time at which to deliver a pacing pulse to the atrium based on the length of the interval and control the signal generator module to deliver the pacing pulse at the scheduled time. The housing is configured for implantation within the atrium. The housing encloses the stimulation generator and the processing module.

25 Claims, 11 Drawing Sheets

(56) References Cited

U.S. PATENT DOCUMENTS

| | | |
|---|---|---|
| 6,788,971 B1 | 9/2004 | Sloman et al. |
| 6,934,585 B1 | 8/2005 | Schloss et al. |
| 7,610,092 B2 | 10/2009 | Cowan et al. |
| 7,937,148 B2 | 5/2011 | Jacobson |
| 8,032,219 B2 | 10/2011 | Neumann et al. |
| 2001/0010009 A1* | 7/2001 | Bakels ................ A61N 1/3622 607/9 |
| 2002/0082648 A1* | 6/2002 | Kramer ............... A61N 1/3622 607/9 |
| 2002/0082659 A1* | 6/2002 | Stahmann ........... A61N 1/3622 607/9 |
| 2002/0120301 A1* | 8/2002 | Levine ................ A61N 1/3622 607/9 |
| 2006/0241705 A1* | 10/2006 | Neumann et al. ................ 607/9 |
| 2007/0088394 A1 | 4/2007 | Jacobson |
| 2007/0088398 A1 | 4/2007 | Jacobson |
| 2007/0093872 A1* | 4/2007 | Chirife et al. .................... 607/9 |
| 2007/0135882 A1* | 6/2007 | Drasler ............... A61B 5/6848 607/126 |
| 2007/0293900 A1 | 12/2007 | Sheldon et al. |
| 2007/0299475 A1 | 12/2007 | Levin et al. |
| 2008/0027490 A1 | 1/2008 | Sheldon et al. |
| 2008/0154322 A1 | 6/2008 | Jackson et al. |
| 2009/0234411 A1 | 9/2009 | Sambelashvili et al. |
| 2013/0116738 A1* | 5/2013 | Samade et al. .................. 607/3 |

OTHER PUBLICATIONS (PCT/US2013/065518) PCT Notification of Transmittal of the International Search Report and the Written Opinion of the International Searching Authority.

(PCT/US2013/065491) PCT Notification of Transmittal of the International Search Report and the Written Opinion of the International Searching Authority.

Response to Office Action dated May 14, 2014, from U.S. Appl. No. 13/665,492, filed Aug. 13, 2014, 18 pp.

Final Office Action from U.S. Appl. No. 13/665,492, dated May 14, 2014, 11 pp.

Notice of Allowance from U.S. Appl. No. 13/665,492, dated Aug. 22, 2014, 8 pp.

Chinese office action, application No. 201380055855.8, dated May 5, 2016, English translation, 5 pages.

Chinese office action, application No. 201380055855.8, dated May 5, 2016, Chinese language, 8 pages.

\* cited by examiner

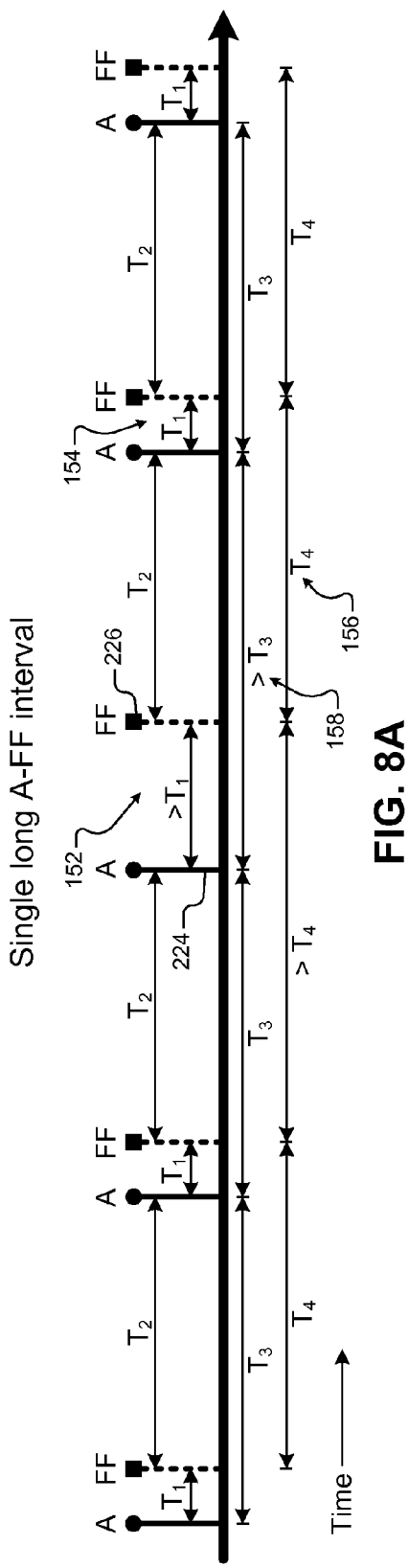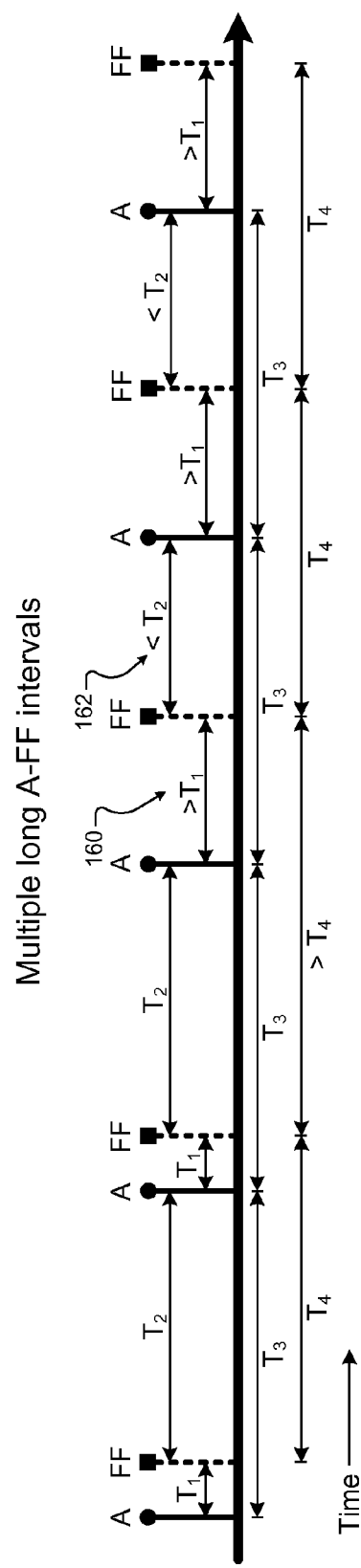

LEADLESS PACEMAKER SYSTEM

TECHNICAL FIELD

The disclosure relates to cardiac pacing, and more particularly, to techniques for cardiac pacing using a leadless pacemaker device.

BACKGROUND

An implantable pacemaker may deliver pacing pulses to a patient's heart and monitor conditions of the patient's heart. The implantable pacemaker may comprise a pulse generator and one or more electrical leads. The pulse generator may be implanted in a small pocket in the patient's chest in some examples. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) where electrodes at the distal ends of the electrical leads connect to the target site. The pulse generator may provide electrical stimulation to the target site and/or monitor cardiac electrical activity at the target site via the electrodes.

In some examples, a leadless pacemaker may be used to sense electrical activity and/or deliver therapeutic signals to the heart. The leadless pacemaker may include one or more electrodes on its outer housing to deliver therapeutic electrical signals and/or sense intrinsic depolarizations of the heart. The leadless pacemaker may be positioned within or outside of the heart and, in some examples, may be anchored to a wall of the heart via a fixation mechanism.

SUMMARY

A leadless atrial pacing device (hereinafter "atrial device") of the present disclosure is configured for implantation within the atrium of a patient's heart. The atrial device may pace the atrium, sense intrinsic atrial electrical activity, and detect ventricular activation. The atrial device may be configured to detect ventricular activation by detecting ventricular electrical activity and/or mechanical contraction of the ventricles. The atrial device may control the timing of pacing pulses delivered to the atrium based on when ventricular activation is detected.

The atrial device may operate as the sole pacing device implanted in the heart in some examples. In other examples, the atrial device may operate along with a leadless ventricular pacing device (hereinafter "ventricular device") that is configured for implantation within a ventricle of the patient's heart. The ventricular device may be configured to sense intrinsic ventricular depolarizations and pace the ventricle. In some examples, the ventricular device may be programmed such that the ventricular device paces at a backup pacing rate (e.g., less than the atrial pacing rate) for situations in which atrial depolarization does not precipitate a ventricular depolarization, e.g., during AV block.

The combination of the atrial and ventricular devices may be referred to herein as a leadless pacing system. The atrial device of the present disclosure may operate reliably without modification (e.g., reprogramming) when the ventricular device has been added to the patient's heart to form a leadless pacing system. The atrial device may operate reliably even when the ventricular device is added because the atrial device controls atrial pacing timing based on sensed ventricular activation, independent on the origin of the sensed ventricular activation. Accordingly, the atrial device of the present disclosure may function in a variety of different scenarios without modification, e.g., as a stand-alone pacing device or implanted along with another pacing device.

The leadless pacing system may coordinate pacing of the heart based on sensed cardiac electrical and/or mechanical activity without establishment of a communication link between the atrial device and the ventricular device. In this manner, the atrial device and the ventricular device may operate independently from one another in the sense that operation of the atrial and ventricular devices may depend on sensed cardiac activity (electrical or mechanical) and may not need to rely on wired or wireless communication, unlike typical pacemakers including pulse generators and electrical leads. Since the atrial device and the ventricular device do not rely on communication to coordinate pacing of the heart, the atrial and ventricular devices may save power that otherwise would be used to coordinate operation of the devices via communication.

In some examples, a device according to the present disclosure comprises a signal generator module, a processing module, and a housing. The signal generator module is configured to deliver pacing pulses to an atrium. The processing module is configured to detect a ventricular activation event and determine a length of an interval between the ventricular activation event and a previous atrial event that preceded (e.g., precipitated) the ventricular activation event. The processing module is further configured to schedule a time at which to deliver a pacing pulse to the atrium based on the length of the interval and control the signal generator module to deliver the pacing pulse at the scheduled time. The housing is configured for implantation within the atrium. The housing encloses the stimulation generator and the processing module.

In some examples, a method according to the present disclosure comprises detecting a ventricular activation event using an atrial pacing device configured for implantation within an atrium and determining a length of an interval between the ventricular activation event and a previous atrial event that preceded the ventricular activation event. The method further comprises scheduling a time at which to deliver a pacing pulse to the atrium based on the length of the interval and delivering the pacing pulse at the scheduled time.

In some examples, a device according to the present disclosure comprises a signal generator module, a processing module, and a housing. The signal generator module is configured to deliver pacing pulses to an atrium. The processing module is configured to detect a far-field R-wave (FFRW) and determine a length of an interval between the detected FFRW and a previous atrial event that preceded the FFRW. The processing module is further configured to schedule a time at which to deliver a pacing pulse to the atrium based on the length of the interval and control the signal generator module to deliver the pacing pulse at the scheduled time. The housing is configured for implantation within the atrium. The housing encloses the stimulation generator and the processing module.

In some examples, a device according to the present disclosure comprises a signal generator module, a processing module, and a housing. The signal generator module is configured to deliver pacing pulses to an atrium. The processing module is configured to detect an S1 heart sound and determine a length of an interval between the detected S1 heart sound and a previous atrial event that preceded the S1 heart sound. The processing module is further configured to schedule a time at which to deliver a pacing pulse to the atrium based on the length of the interval and control the signal generator module to deliver the pacing pulse at the scheduled time. The housing is configured for implantation within the atrium. The housing encloses the stimulation generator and the processing module.

In some examples, a system according to the present disclosure comprises a ventricular pacing device and an atrial pacing device. The ventricular pacing device is configured for implantation within a ventricle of a heart. The ventricular pacing device is further configured to deliver pacing pulses to the ventricle. The atrial pacing device is configured for implantation within an atrium of the heart. The atrial pacing device is further configured to detect a ventricular activation event and deliver pacing pulses to the atrium based on when the ventricular activation event is detected.

In some examples, a method according to the present disclosure comprises delivering pacing pulses to a ventricle of a heart using a ventricular pacing device configured for implantation within the ventricle. The method further comprises detecting a ventricular activation event using an atrial pacing device configured for implantation within an atrium of the heart. Additionally, the method comprises delivering pacing pulses to the atrium based on when the ventricular activation event is detected.

In some examples, a device according to the present disclosure comprises a signal generator module, a processing module, and a housing. The signal generator module is configured to deliver pacing pulses to an atrium. The processing module is configured to detect a first ventricular activation event, detect a second ventricular activation event subsequent to the first ventricular activation event, and determine a length of an interval between the first and second ventricular activation events. The processing module is further configured to schedule a time at which to deliver a pacing pulse to the atrium based on the length of the interval and control the signal generator module to deliver the pacing pulse at the scheduled time. The housing is configured for implantation within the atrium. The housing encloses the stimulation generator and the processing module.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 8A-8B are example atrial pacing timing diagrams including long intervals between atrial events and subsequently detected far-field R-waves.

DETAILED DESCRIPTION

Figure 1:
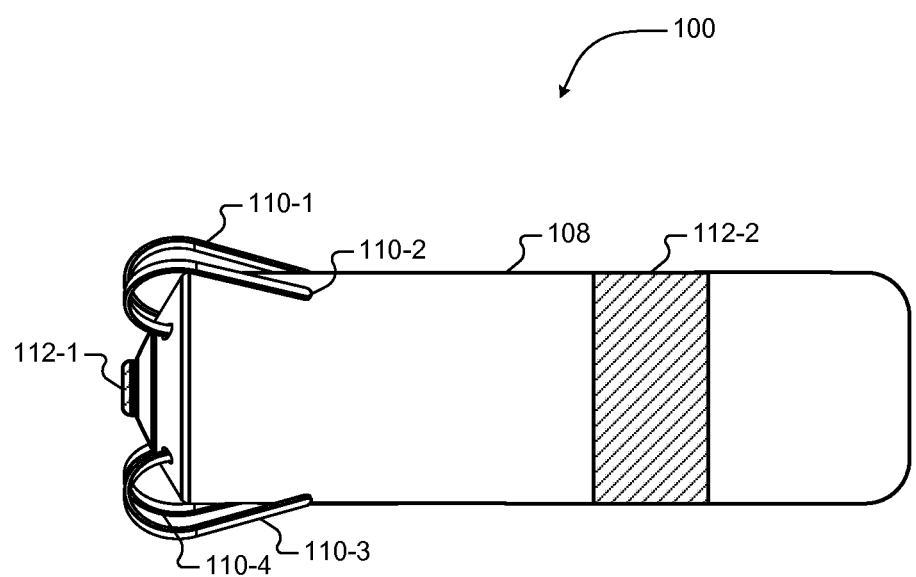
FIG. 1 shows an example leadless pacemaker device.

An implantable atrial pacing device (hereinafter "atrial device") of the present disclosure is configured for implantation within the atrium of a patient's heart. The atrial device may pace the atrium, sense intrinsic atrial electrical activity, and detect ventricular activation. The atrial device may control the timing of pacing pulses delivered to the atrium based on the detected ventricular activity.

The atrial device may include a hermetically sealed housing having a size and form factor that allows the atrial device to be implanted within the atrium. In some examples, the housing may have a cylindrical (e.g., pill-shaped) form factor. The housing may include fixation tines that connect the housing to the cardiac tissue within the atrium. The fixation tines may anchor the atrial device to the atrial cardiac tissue such that the atrial device moves along with the atrial cardiac tissue during cardiac contractions.

The housing of the atrial device may house components for sensing cardiac electrical activity such as intrinsic atrial depolarizations and ventricular depolarizations, e.g., far-field R-waves (FFRWs). The atrial device may also house components for delivering electrical stimulation therapy, such as pacing pulses. In some examples, the atrial device may also house components for sensing physiological parameters, such as acceleration, pressure, sound, and/or impedance.

The atrial device may include a plurality of electrodes used for sensing cardiac electrical activity and delivering electrical stimulation therapy (e.g., pacing pulses). For example, the atrial device may include a tip electrode and a ring electrode. The tip electrode may be located on the housing such that the tip electrode contacts the cardiac tissue when the atrial device is anchored to the cardiac tissue by the fixation tines. The ring electrode may also be located on the housing. For example, the ring electrode may be disposed around the circumference of the housing.

The atrial device may be configured to detect ventricular activation events. Ventricular activation may generally refer to electrical depolarization of the ventricular cardiac tissue and the subsequent mechanical contraction of the ventricular cardiac tissue. The atrial device may be configured to detect ventricular activation based on the detection of ventricular electrical activity and/or based on the detection of mechanical contraction of the ventricles. As used herein, detection of ventricular activation may generally refer to the detection of ventricular electrical activity (e.g., FFRWs) and/or the detection of mechanical contraction of the ventricles (e.g., based on heart sounds). In some examples, the atrial device may detect ventricular activation by detecting FFRWs. In some examples, the atrial device may detect ventricular activation by detecting S1 heart sounds. Although the atrial device may detect ventricular activation based on FFRWs and/or heart sounds, it is contemplated that the atrial device may detect ventricular activation using other sensors and techniques.

In some examples, the atrial device may detect FFRWs in the atrium which are indicative of a ventricular depolarization. For example, the atrial device may detect FFRWs and determine when ventricular depolarization has occurred based on the detection of FFRWs. Although the atrial device is described herein as detecting ventricular depolarization based on the detection of FFRWs, it is contemplated that the atrial device may detect ventricular depolarization based on detected ventricular electrical activity other than FFRWs.

Additionally, or alternatively, the atrial device may be configured to detect mechanical contraction of the ventricles. For example, the atrial device may detect physiological parameters other than cardiac electrical activity, such as acceleration and/or pressure. In some examples, the atrial device may include one or more sensors that measure acceleration and/or pressure in the atrium. In these examples, the atrial device may detect mechanical contraction of the ventricles based on signals generated by the one or more sensors. For example, the atrial device may detect S1 heart sounds indicative of closure of the atrioventricular valves at the beginning of ventricular contraction and then determine that ventricular contraction has occurred based on the detection of S1 heart sounds. Additionally, or alternatively, the atrial device may detect S2 heart sounds in some examples, and then determine that ventricular contraction has occurred based on the detection of S2 heart sounds.

The atrial device may control atrial pacing timing based on when ventricular activation is detected during a cardiac cycle. In some examples, the atrial device may determine when to pace the atrium based on when FFRWs are detected during the cardiac cycle. Additionally, or alternatively, the atrial device may determine when to pace the atrium based on when S1 heart sounds are detected during the cardiac cycle. A cardiac cycle may refer to cardiac electrical activity that occurs from the beginning of one heartbeat to the beginning of the next heartbeat, as sensed by electrodes and/or sensors of the atrial device. Components of the atrial device that sense cardiac electrical activity, sense contraction of the ventricles, and control the delivery of electrical stimulation to the atrium are described hereinafter.

The atrial device may include an electrical sensing module (i.e., sensing module) that is configured to monitor cardiac electrical activity in the atrium. The sensing module may include electronic components that acquire cardiac electrical signals via the electrodes of the atrial device (e.g., the tip and ring electrodes). In some examples, the sensing module may implement signal conditioning on the acquired electrical signals. For example, the sensing module may filter, amplify, and digitize the acquired electrical signals. The electrical activity monitored by the sensing module may include a variety of different electrical signal components. The electrical activity may include intrinsic cardiac electrical activity, e.g., intrinsic atrial activity and/or intrinsic ventricular electrical activity, or other electrical signals.

The atrial device may include one or more sensors, such as an accelerometer and/or a pressure sensor. An accelerometer included in the atrial device may generate signals that indicate the acceleration of the atrial device. A pressure sensor included in the atrial device may generate signals that indicate pressure within the atrium. When the atrial device includes a pressure sensor or an accelerometer, the atrial device may detect ventricular activation based on signals generated by the sensors. For example, as described above, the atrial device may detect contraction of the ventricles based on sensor signals indicative of ventricular contraction, such as S1 heart sounds.

The atrial device may include a stimulation generator module (i.e., "stimulation generator") that is configured to deliver electrical stimulation to the atrium via the electrodes (e.g., the tip and ring electrodes). For example, the atrial device may deliver pacing pulses to the atrium via the electrodes. In some examples, the atrial device may deliver electrical stimulation other than pacing pulses, such as anti-tachycardia pacing (ATP) therapy.

The atrial device may include a processing module that receives sensing data from the sensing module. The data received from the sensing module may include digitized electrical activity that was received via the electrodes of the atrial device. The processing module may detect intrinsic atrial activity based on the sensing data received from the sensing module. For example, the processing module may detect an intrinsic atrial depolarization based on the sensing data received from the sensing module. Detection of intrinsic atrial depolarization by the processing module may be referred to as an "atrial sensed event" or a "sensed atrial event" in some examples. Atrial electrical activity that is precipitated by delivery of a pacing pulse from the stimulation generator may be referred to as an "atrial paced event."

The processing module may detect ventricular activation events in a variety of different ways. In some examples, the processing module may detect ventricular electrical activity (e.g., FFRWs). In some examples, the processing module may detect ventricular contraction based on signals received from the one or more sensors included in the atrial device. For example, the processing module may detect heart sounds (e.g., the S1 heart sound) based on the signals received from the one or more sensors and detect ventricular contractions based on the detected heart sounds. Heart sounds may be mechanical perturbations generated during contractions of the heart, such as blood flow and the closing of heart valves. The sensors (e.g., acceleration and/or pressure sensors) may generate signals in response to the mechanical perturbations. Heart sounds may be referred to as S1, S2, S3, or S4 heart sounds, for example. The S1 heart sound may be caused by closure of the atrioventricular valves, e.g., the tricuspid and/or mitral valves at the beginning of ventricular contraction. As such, the S1 heart sound may indicate ventricular contraction. The processing module may also detect heart sounds S2, S3, and S4 in some examples, and determine other cardiac parameters based on the detected heart sounds.

As described above, the processing module may detect ventricular activation based on the detection of ventricular electrical activity (e.g., FFRWs) and/or based on the detection of other ventricular contractions (e.g., S1 heart sounds). In some examples, the processing module may detect ventricular activation based only on detected ventricular electrical activity. In other examples, the processing module may detect ventricular activation based only on the detection of ventricular contractions, e.g., based only on accelerometer data and/or pressure data. In still other examples, the processing module may detect ventricular activation based on a combination of both ventricular electrical activity and detected ventricular contractions, e.g., both FFRWs and S1 heart sounds.

The processing module may control when the stimulation generator delivers pacing pulses (i.e., atrial pacing timing) based on when the processing module detects ventricular activation during a cardiac cycle. For example, the processing module may first determine an amount of time between a ventricular activation event and a previous atrial event (e.g., an intrinsic or paced atrial event) that preceded the detected ventricular activation event. Then, the processing module may schedule a time at which to deliver a pacing pulse to the atrium based on the determined amount of time between the ventricular activation event and the previous atrial event. The processing module may then control the signal generator module to deliver the pacing pulse to the atrium at the scheduled time. In some examples, the processing module may be configured to inhibit delivery of a pacing pulse at the scheduled time if the processing module senses an intrinsic atrial depolarization before the scheduled time at which the pacing pulse was to be delivered.

The processing module may control atrial pacing timing based on the detection of ventricular activation in a variety of different ways. The manner in which the processing module controls atrial pacing timing may depend on when ventricular activation occurs relative to the atrial event that preceded (e.g., precipitated) the ventricular activation. For example, the manner in which the processing module controls atrial pacing timing may depend on when a FFRW is sensed relative to the atrial event that preceded the FFRW. As another example, the manner in which the processing module controls atrial pacing timing may depend on when an S1 heart sound is sensed relative to the atrial event that preceded the contraction causing the sensed S1 heart sound.

Figure 4:
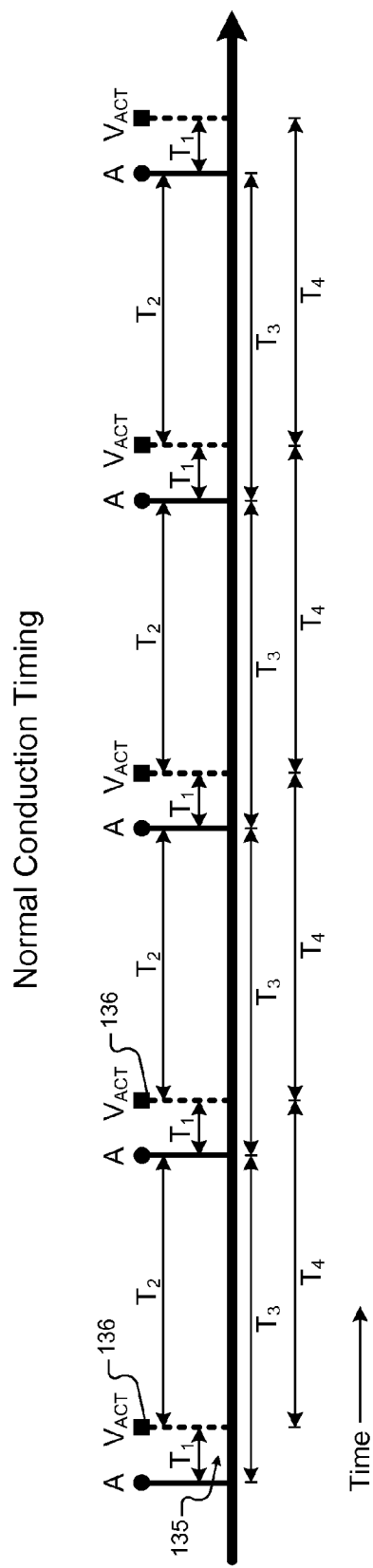
FIG. 4 is an example atrial pacing timing diagram during normal atrioventricular (AV) conduction that includes ventricular activation ($V_{ACT}$) markers.

The amount of time between an atrial event (paced or sensed) and a subsequent ventricular activation event preceded by the atrial event may be generally referred to herein as an "A-$V_{ACT}$ interval." Accordingly, the processing module may control atrial pacing timing based on the value of the A-$V_{ACT}$ interval. An A-$V_{ACT}$ interval is illustrated as 135 in FIG. 4. In FIG. 4, the A-$V_{ACT}$ interval has a value of T1 seconds. In examples where the processing module detects FFRWs, the amount of time between the atrial event and subsequent detection of a FFRW may be referred to herein as an "A-FF interval." In these examples, the processing module may control atrial pacing timing based on the value of the A-FF interval. FIGS. 6-10 illustrate various different A-FF intervals, which may depend on various different heart conditions and/or pacing programs implemented by the processing module.

As described above, the processing module may control atrial pacing timing based on the length of the A-$V_{ACT}$ interval. In some examples, A-$V_{ACT}$ intervals may be approximately equal over a plurality of cardiac cycles. In other examples, A-$V_{ACT}$ intervals may vary over a plurality of cardiac cycles. For example, for two consecutive cardiac cycles, the A-$V_{ACT}$ interval of the second cardiac cycle may be different than the A-$V_{ACT}$ interval of the first cardiac cycle. The processing module may control atrial pacing timing during a single cardiac cycle based on the A-$V_{ACT}$ interval associated with that single cardiac cycle in some examples. In other examples, the processing module may control atrial pacing timing based on a plurality of A-$V_{ACT}$ intervals that have occurred over a plurality of previous cardiac cycles.

The processing module may control atrial pacing timing in different ways depending on the duration of the A-$V_{ACT}$ interval. In general, the A-$V_{ACT}$ interval may be characterized as having a normal duration, a short duration, or a long duration. Operation of the atrial device in response to normal A-$V_{ACT}$ intervals is illustrated in FIG. 4. Operation of the atrial device in response to normal A-FF intervals, short A-FF intervals, and long A-FF intervals is illustrated in FIGS. 6-8B. Although FIGS. 6-10 illustrate atrial pacing timing based on the detection of FFRWs, the timing diagrams of FIGS. 6-10 may be generally applicable to scenarios in which ventricular activation is detected using other techniques. For example, the timing diagrams of FIGS. 6-10 may be similar to timing diagrams in cases where the processing module controls atrial pacing timing based on S1 heart sounds. In one example, timing diagrams showing operation of the atrial device using S1 heart sounds instead of FFRWs may include S1 markers indicating when S1 heart sounds are detected instead of FF symbols indicating when FFRWs are detected. Accordingly, although the timing diagrams of FIGS. 6-10, illustrating detection of FFRWs, are used to describe the operation of the atrial device, the atrial device of the present disclosure may operate in a similar manner as illustrated in FIGS. 6-10 when detecting ventricular activation using other techniques, such as using S1 heart sounds.

In general, during normal AV conduction in the heart, the processing module may control the stimulation generator to deliver pacing pulses at a baseline atrial pacing rate (e.g., 60 bpm) such that the intervals between atrial events are approximately equal over a plurality of cardiac cycles. Normal AV conduction in the heart may refer to the scenario in which there is normal electrical continuity between the atria and ventricles. During normal AV conduction in the heart, the A-$V_{ACT}$ interval may be characterized as having a normal duration. Normal duration for the A-$V_{ACT}$ interval when the heart is being paced at 60 beats per minute (bpm) may be approximately 250-350 ms. For example, the delay between the atrial event and ventricular activation may be approximately 150 ms, while the delay from ventricular activation to detection of the ventricular activation, e.g., via detection of a FFRW, may be approximately 100 ms. The delay from ventricular activation to the detection of ventricular activation by the atrial device may be characterized on a per-patient basis in some examples. Accordingly, normal, short, and long A-$V_{ACT}$ intervals described herein may be set on a per-patient basis in some examples.

Figure 6:
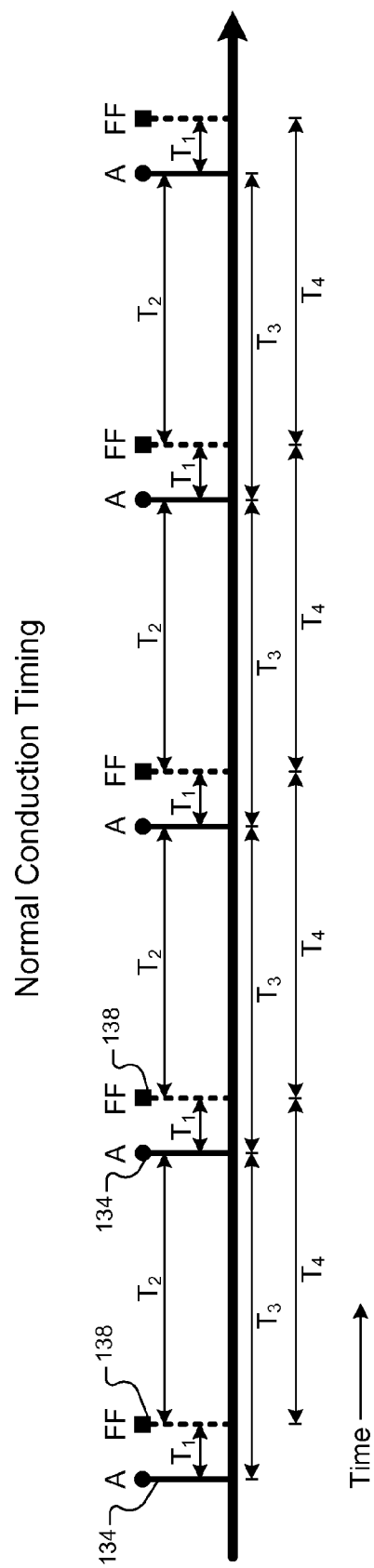
FIG. 6 is an example atrial pacing timing diagram during normal AV conduction that includes detected far-field R-waves.

FIG. 4 illustrates atrial pacing timing based on detected ventricular activations (e.g., FFRWs or S1 heart sounds) during normal AV conduction. In FIG. 4, the A-$V_{ACT}$ (e.g., A-FF) interval has a consistent value of T1, while the intervals between consecutive atrial events (i.e., the A-A interval) consistently have a value of T3. The processing module may set the pacing pulse to occur a period of time after detection of ventricular activation. For example, during normal AV conduction (e.g., when the A-$V_{ACT}$ interval is approximately equal to T1), the processing module may set a pacing pulse to occur T2 seconds after the detected ventricular activation. Similarly, when processing module controls atrial pacing timing based on the detection of FFRWs, the processing module may set pacing pulses to occur approximately T2 seconds after a detected FFRW, as illustrated in FIG. 6.

The processing module may control the duration of time between the detection of ventricular activation and the delivery of the next pacing pulse. For example, when the processing module detects an A-$V_{ACT}$ interval having a duration T1 (i.e., a normal AV interval), the processing module may set the atrial pacing pulse to occur at a time that is approximately T2 seconds after the detected $V_{ACT}$. The processing module may determine the value T2 based on a baseline atrial pacing interval value (e.g., T3) and the length of the A-$V_{ACT}$ interval (e.g., T1). The baseline atrial pacing interval T3 may be an interval stored in memory of the atrial device, which may be updated over time in some examples. The baseline atrial pacing interval may be the reciprocal value of the baseline atrial pacing rate (e.g., 60 bpm). During normal AV conduction where the A-$V_{ACT}$ interval has a normal duration of T1, the processing module may schedule pacing pulses such that atrial events are separated by the baseline atrial pacing interval. The processing module may update the baseline pacing rate (or interval) over time based on a variety of factors, such as an activity level of the patient. For example, the processing module may set the baseline atrial pacing rate at approximately 60 bpm when the patient is at rest and then increase the baseline atrial pacing rate to a value greater than 60 bpm when the processing module determines that a patient is active (e.g., based on signals from an activity sensor).

During normal AV conduction, the processing module may determine the $V_{ACT}$-A interval (i.e., T2), and, therefore, when the pacing pulse is to be delivered, by subtracting the A-$V_{ACT}$ interval (e.g., T1) from the baseline atrial pacing interval (e.g., T3). For example, assuming that ventricular activation is detected T1 seconds after an atrial event (sensed or paced), the processing module may subtract the A-$V_{ACT}$ interval of T1 from the baseline atrial pacing interval T3 to determine the value T2. The processing module may then control the stimulation generator to deliver a pacing pulse that occurs T2 seconds after the detection of ventricular activation. In this manner, during normal AV conduction over a plurality of cardiac cycles, the processing module may control the stimulation generator to deliver pacing pulses such that the baseline atrial pacing rate is maintained over the plurality of cardiac cycles.

The timing between ventricular activation and the atrial event that preceded the ventricular activation may deviate from the normal A-$V_{ACT}$ interval in a variety of ways. In some examples, the A-$V_{ACT}$ interval may be shortened (e.g., the A-FF interval is less than T1). The A-$V_{ACT}$ interval (e.g., A-FF interval or A-S1 interval) may be shortened in some examples due to a premature ventricular contraction (PVC). In other examples, the A-$V_{ACT}$ interval may be lengthened (e.g., the A-FF interval is greater than T1). The A-$V_{ACT}$ interval (e.g., A-FF interval or A-S1 interval) may be lengthened in some examples due to AV block.

A normal A-$V_{ACT}$ interval may be stored in memory. A normal A-$V_{ACT}$ interval or normal A-FF interval may be referred to herein as a "baseline AV value" in some examples because the normal A-$V_{ACT}$ interval or normal A-FF interval may be the expected value of the interval between an atrial event and a ventricular activation during normal AV conduction in the heart. The normal A-$V_{ACT}$ interval (i.e., baseline AV value) may be associated with the baseline atrial pacing interval in memory. For example, a normal A-$V_{ACT}$ interval may be approximately 250 ms when the baseline atrial pacing interval is 1000 ms (i.e., an atrial rate of 60 bpm). The baseline AV value may be updated along with the baseline atrial pacing interval in some examples. In general, the baseline AV value may be shortened/lengthened during periods of detected exercise/relaxation in examples where the atrial device is configured to detect the activity level of the patient, e.g., using an activity sensor.

In some examples, the processing module may determine that the A-$V_{ACT}$ interval is a short A-$V_{ACT}$ interval when the A-$V_{ACT}$ interval is shorter than the normal A-$V_{ACT}$ interval by a threshold amount of time. Similarly, the processing module may determine that the A-$V_{ACT}$ interval is a long A-$V_{ACT}$ interval when the detected A-$V_{ACT}$ interval is longer than a normal A-$V_{ACT}$ interval by a threshold amount of time.

In other examples, ventricular activation may go undetected during some cardiac cycles. The A-$V_{ACT}$ interval may go undetected when the processing module does not detect a FFRW, e.g., because of a weak electrical signal or excessive noise, or because AV block has caused no $V_{ACT}$ to occur. For example, the processing module may determine that ventricular activation is not detected during a cardiac cycle when ventricular activation has not been detected within a threshold amount of time after an atrial event. In still other examples, the processing module may detect multiple ventricular activations subsequent to a single atrial event before another atrial event is detected. Multiple ventricular activations may be detected after a single atrial event in some examples due to PVCs.

Operation of the atrial device during short A-$V_{ACT}$ intervals, long A-$V_{ACT}$ intervals, undetected ventricular activations, and multiple ventricular activations is described hereinafter. Description of atrial pacing timing based on the detection of FFRWs in response to short A-FF intervals, long A-FF intervals, undetected FFRWs, and multiple FFRWs is described in detail with respect to FIGS. 6-10.

Figure 7A:
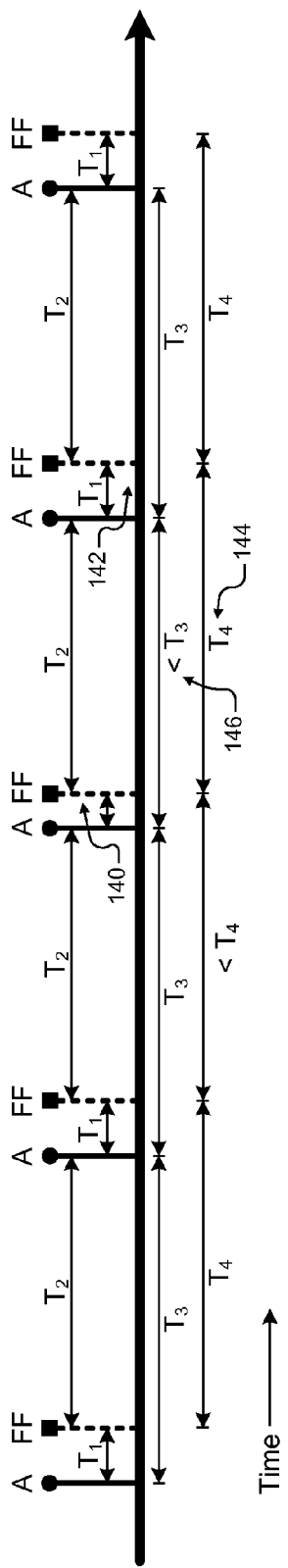
FIGS. 7A-7B are example atrial pacing timing diagrams including short intervals between atrial events and subsequently detected far-field R-waves.

In examples where the processing module detects a short A-$V_{ACT}$ interval, the processing module may maintain the normal $V_{ACT}$-A interval timing (e.g., T2) such that the $V_{ACT}$-$V_{ACT}$ interval will be maintained during the subsequent cardiac cycle, assuming the A-$V_{ACT}$ interval of the subsequent cycle returns to the normal duration of T1. FIG. 7A shows an example in which the processing module detects a shortened A-FF interval at 140 and maintains the FF-A interval such that the FF-FF interval is maintained. In FIG. 7A, the A-FF interval returns to the normal duration after the shortened A-FF interval. Maintaining the $V_{ACT}$-$V_{ACT}$ interval may promote regular $V_{ACT}$-$V_{ACT}$ timing which may cause a smoothing of the ventricular rate. In examples where a ventricular pacing device (e.g., ventricular device 200 of FIGS. 11-12) is implanted in a patient, the ventricular pacing device may not have knowledge of a short A-$V_{ACT}$ interval. In these examples, having the atrial device pacing to maintain $V_{ACT}$-$V_{ACT}$ timing may help keep the atrial and ventricular devices in synch.

Maintaining the $V_{ACT}$-A interval after a shortened A-$V_{ACT}$ interval may tend to decrease the length of the interval between atrial events. In other words, maintaining the $V_{ACT}$-A interval after a shortened A-$V_{ACT}$ interval may increase the atrial rate of the patient to a rate that is greater than the baseline atrial pacing rate. In order to bring the patient's heart rate back to the baseline atrial pacing rate in cases where the A-$V_{ACT}$ interval is shortened for a plurality of cardiac cycles, the processing module may extend the $V_{ACT}$-A interval to a value that is greater than T2. In some examples, the processing module may maintain the $V_{ACT}$-A interval at a value of T2 seconds over a plurality of cardiac cycles having shortened A-$V_{ACT}$ intervals until it becomes apparent that the shortened A-$V_{ACT}$ interval will likely persist. If the processing module determines that a shortened A-$V_{ACT}$ interval is likely to persist, then the processing module may lengthen the $V_{ACT}$-A interval (e.g., to a value of greater than T2) in order to maintain the baseline atrial pacing interval T3 during subsequent cardiac cycles such that the patient's heart rate is maintained at the baseline atrial pacing rate. In some examples, the processing module may determine that the short A-$V_{ACT}$ interval is persistent if greater than a threshold number of cardiac cycles include short A-$V_{ACT}$ intervals. For example, the processing module may determine that the short A-$V_{ACT}$ interval may persist if greater than a threshold number of consecutive A-$V_{ACT}$ intervals are short.

In examples where the processing module detects a long A-$V_{ACT}$ interval (e.g., greater than T1), the processing module may maintain the normal $V_{ACT}$-A interval timing (e.g., T2) such that the $V_{ACT}$-$V_{ACT}$ interval will be maintained during the subsequent cardiac cycle, assuming the A-$V_{ACT}$ interval of the subsequent cardiac cycle returns to the normal A-$V_{ACT}$ interval length. In some examples, the A-$V_{ACT}$ interval may return to the normal length in a subsequent cardiac cycle, thereby maintaining the patient's ventricular rate. However, in other examples, the A-$V_{ACT}$ interval may not return to normal. Instead, the long A-$V_{ACT}$ interval may persist for a plurality of cardiac cycles.

In some examples, the processing module may maintain the normal $V_{ACT}$-A interval over a plurality of cardiac cycles having long A-$V_{ACT}$ intervals until it becomes apparent that the long A-$V_{ACT}$ intervals will likely persist. If the processing module determines that a long A-$V_{ACT}$ interval is likely to persist, then the processing module may shorten the $V_{ACT}$-A intervals (e.g., to a value less than T2) in order to maintain the baseline atrial pacing interval during subsequent cardiac cycles. In some examples, the processing module may determine that the long A-$V_{ACT}$ intervals will likely persist if greater than a threshold number of cardiac cycles include long A-$V_{ACT}$ intervals. For example, the processing module may determine that the long A-$V_{ACT}$ interval condition may persist if greater than a threshold number of consecutive A-$V_{ACT}$ intervals are long.

In some examples, ventricular activation may go undetected subsequent to an atrial event. The processing module may make the determination that ventricular activation has gone undetected after an atrial event when the processing module has not detected ventricular activation (e.g., a FFRW) within a threshold amount of time after an atrial event. The threshold amount of time may be an amount of time in which a ventricular activation should likely have been detected during normal or long A-$V_{ACT}$ intervals. For example, the threshold amount of time may be set to a value that is greater than an expected long A-$V_{ACT}$ interval, e.g., within approximately 400 ms of the atrial event. In examples where the processing module determines that ventricular activation has went undetected, the processing module may schedule the subsequent atrial pace in a manner that maintains the baseline atrial pacing interval. For example, the processing module may set the atrial pace to occur T3 seconds after the last detected atrial event when the processing module determines that ventricular activation went undetected subsequent to the last atrial event.

In some examples, the processing module may detect multiple ventricular activations after an atrial event. In these examples, the processing module may adjust atrial pacing timing in order to prevent pacing against closed AV valves, which may create patient symptoms. For example, upon detection of multiple ventricular activations subsequent to a single atrial event, the processing module may delay atrial pacing such that atrial pacing occurs a period of time after the last of the detected ventricular activations such that the atrium is not paced while the AV valves are closed.

The atrial device of the present disclosure may operate as a stand alone implantable device. In other words, the atrial device may operate as the sole pacing device implanted in the heart in some examples. Although the atrial device may operate as the sole pacing device implanted within the heart, in other examples, the atrial device may operate along with an implanted leadless ventricular pacing device (hereinafter "ventricular device"). The ventricular device of the present disclosure may be implanted within a ventricle of the heart, sense ventricular depolarization, and pace the ventricle. The combination of the atrial and ventricular devices may be referred to herein as a leadless pacing system (e.g., leadless pacing system 202 of FIG. 11).

In some examples the atrial and ventricular devices may be implanted into the patient at the same time, e.g., during the same implant procedure. In other examples, the ventricular device may be implanted at a later time. For example, the patient may initially have the atrial device implanted to treat sick sinus syndrome (e.g., bradycardia), then have the ventricular device implanted at a later time after the patient develops AV block. In still other examples, the atrial device of the present disclosure may be implanted some time after the ventricular device has already been implanted in an earlier procedure. For example, the atrial device may be implanted after the ventricular device if the patient develops pacemaker syndrome subsequent to implantation of the ventricular pacing device.

The atrial device of the present disclosure may operate reliably without modification when a ventricular device has been added to the patient's heart to form a leadless pacing system. Put another way, the atrial device of the present disclosure may not require modification (e.g., reprogramming) in order to function along with a subsequently implanted ventricular device. The atrial device may operate even when the ventricular device is added because the atrial device controls atrial pacing timing based on sensed ventricular activation, independent on the origin of the sensed ventricular activation. For example, the atrial device may control pacing timing in the manner described herein whether the ventricular activation detected by the atrial device arises due to intrinsic ventricular depolarization or due to ventricular pacing by the ventricular device. Accordingly, the atrial device of the present disclosure may function in a variety of different circumstances without modification, e.g., as a stand-alone device or implanted along with another device.

Although the atrial device of the present disclosure may not require additional programming upon implantation of a ventricular device, in some examples, the ventricular device may be programmed to function along with the atrial device in order to provide more optimal cardiac pacing. Put another way, in some examples, the ventricular device may be configured (e.g., programmed) to operate along with the atrial device in order to assure that the leadless pacing system performs at an optimal level. For example, as described herein, the ventricular device may be programmed such that the ventricular device paces at a backup rate (e.g., less than the atrial pacing rate) for situations in which atrial depolarization does not precipitate a ventricular depolarization, e.g., during AV block. In this example, the ventricular device may pace the ventricle when the ventricular device does not detect intrinsic ventricular depolarization within a period of time, e.g., due to AV block in the heart. Operation of the atrial and ventricular devices is described hereinafter with reference to FIGS. 11-12.

Although the processing module may control atrial pacing timing based on when ventricular activation occurs relative to the atrial event that preceded the ventricular activation, the processing module may control atrial pacing timing based on other measured intervals in some examples. For example, the processing module may control atrial pacing timing based on the amount of time between a first ventricular activation event during a first cardiac cycle and a second ventricular activation event during a second cardiac cycle that occurs subsequent to the first cardiac cycle. The amount of time between two consecutive $V_{ACT}$ events, i.e., the first and second ventricular activation events, may be generally referred to herein as a "$V_{ACT}$-$V_{ACT}$ interval." In this example, the processing module may first determine the amount of time between the first and second ventricular activation events and then schedule an atrial pace based on the amount of time between the first and second ventricular activation events. Although the processing module may control atrial pacing timing based on A-$V_{ACT}$ and $V_{ACT}$-$V_{ACT}$ intervals, it is contemplated that the processing module may additionally or alternatively control atrial pacing timing based on other measured intervals, such as A-A intervals.

The processing module may control atrial pacing timing based on the length of the $V_{ACT}$-$V_{ACT}$ interval in a variety of different ways. In examples where the processing module detects FFRWs, the amount of time between two consecutive ventricular activation events may be referred to herein as an "FF-FF interval." In these examples, the processing module may control atrial pacing timing based on the value of the FF-FF interval. In examples where the processing module detects S1 heart sounds, the amount of time between two consecutive ventricular activation events may be referred to herein as an "S1-S1 interval." In these examples, the processing module may control atrial pacing timing based on the value of the S1-S1 interval.

The processing module may control atrial pacing timing in different ways depending on the duration of the $V_{ACT}$-$V_{ACT}$ interval. The $V_{ACT}$-$V_{ACT}$ interval may be characterized as having a normal duration, a short duration, or a long duration. During normal AV conduction in the heart, the $V_{ACT}$-$V_{ACT}$ interval may be characterized as having a normal duration. A normal $V_{ACT}$-$V_{ACT}$ interval may be stored in memory. The normal $V_{ACT}$-$V_{ACT}$ interval may be the expected value of the interval between two consecutive ventricular activation events during normal AV conduction in the heart. The duration of the $V_{ACT}$-$V_{ACT}$ interval during normal AV conduction may be referred to herein as a "baseline ventricular interval value." Normal duration for the $V_{ACT}$-$V_{ACT}$ interval (i.e., the baseline ventricular interval value) when the heart is being paced at 60 bpm may be approximately 1000 ms. FIG. 4 illustrates atrial pacing timing based on detected ventricular activations (e.g., FFRWs or S1 heart sounds) during normal AV conduction. In FIG. 4, the $V_{ACT}$-$V_{ACT}$ (e.g., FF-FF) interval has a consistent value of T4. During normal AV conduction, when the $V_{ACT}$-$V_{ACT}$ interval has a normal duration, the processing module may schedule the atrial pace to occur T2 seconds after the second detected $V_{ACT}$ event.

The timing between consecutive ventricular activation events may deviate from the normal $V_{ACT}$-$V_{ACT}$ interval. In some examples, the $V_{ACT}$-$V_{ACT}$ interval may be shortened (e.g., the FF-FF interval is less than T4). The $V_{ACT}$-$V_{ACT}$ interval may be shortened in some examples due to a PVC. In some examples, the processing module may determine that the $V_{ACT}$-$V_{ACT}$ interval is a short $V_{ACT}$-$V_{ACT}$ interval when the $V_{ACT}$-$V_{ACT}$ interval is shorter than the normal $V_{ACT}$-$V_{ACT}$ interval by a threshold amount of time. In other examples, the $V_{ACT}$-$V_{ACT}$ interval may be lengthened, e.g., due to AV block. The processing module may determine that the $V_{ACT}$-$V_{ACT}$ interval is a long $V_{ACT}$-$V_{ACT}$ interval when the detected $V_{ACT}$-$V_{ACT}$ interval is longer than a normal $V_{ACT}$-$V_{ACT}$ interval by a threshold amount of time. Operation of the atrial device during normal $V_{ACT}$-$V_{ACT}$ intervals, short $V_{ACT}$-$V_{ACT}$ intervals, and long $V_{ACT}$-$V_{ACT}$ intervals is described herein.

Figure 3:
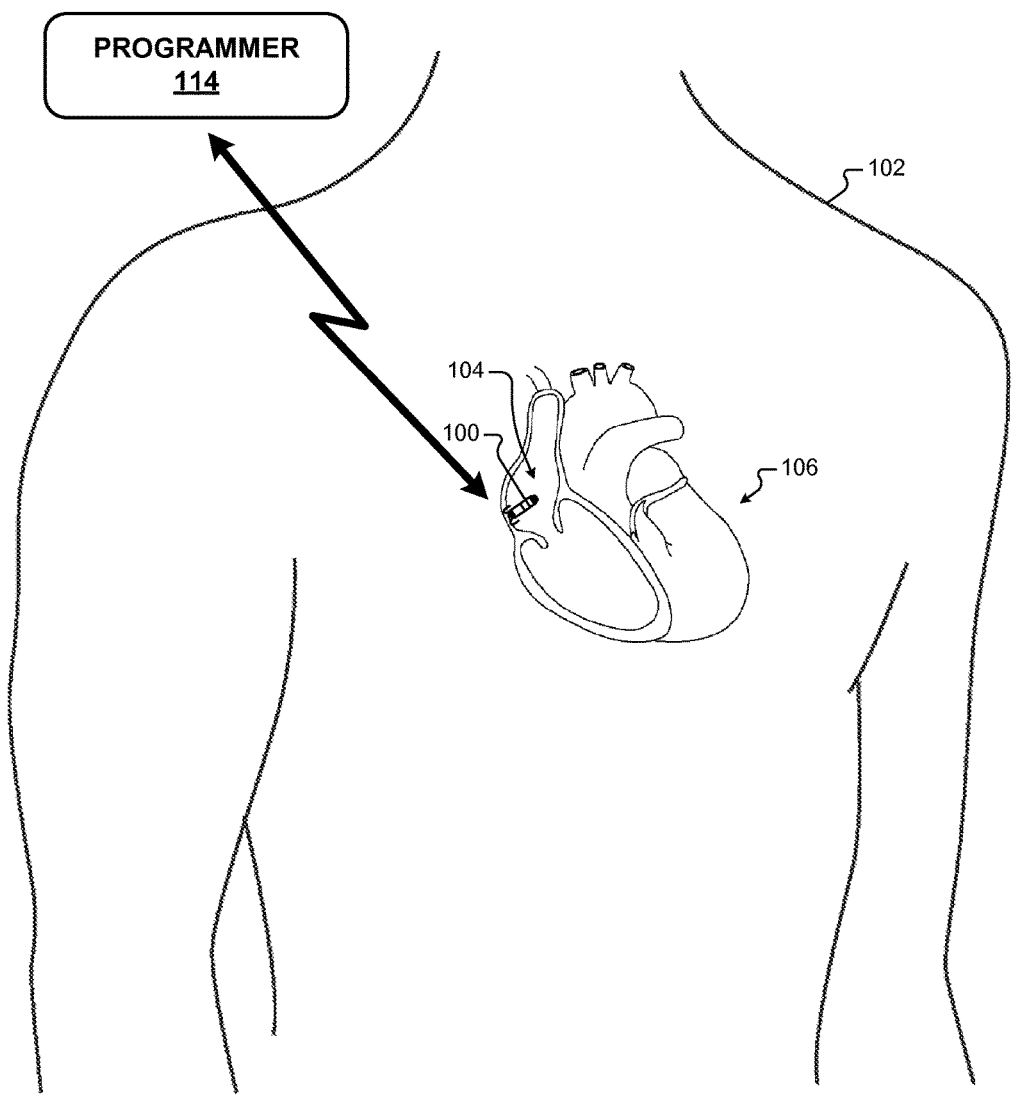
FIG. 3 shows an example leadless pacemaker device implanted in a patient that may be used to diagnose conditions of and provide therapy to a heart of the patient.

FIG. 1 shows a leadless atrial pacemaker device 100 (hereinafter "atrial device 100") that may be configured for implantation in a patient 102 (FIG. 3). For example, atrial device 100 may be configured for implantation within right atrium 104 of patient 102. Atrial device 100 may be configured to monitor electrical activity of heart 106 and/or provide electrical therapy to heart 106.

Atrial device 100 includes a housing 108, fixation tines 110-1, 110-2, 110-3, 110-4 (collectively "fixation tines 110"), and electrodes 112-1, 112-2. Housing 108 may have a pill-shaped cylindrical form factor in some examples. Fixation tines 110 are configured to connect (e.g., anchor) atrial device 100 to heart 106. Fixation tines 110 may be fabricated from a shape memory material, such as Nitinol. In some examples, fixation tines 110 may connect atrial device 100 to heart 106 within one of the chambers of heart 106. For example, as illustrated and described herein with respect to FIG. 3 and FIG. 11, fixation tines 110 may be configured to anchor atrial device 100 to heart 106 within right atrium 104. Although atrial device 100 includes a plurality of fixation tines 110 that are configured to anchor atrial device 100 to cardiac tissue in the right atrium, it is contemplated that a leadless device according to the present disclosure may be fixed to cardiac tissue in other chambers of a patient's heart using other types of fixation mechanisms.

Atrial device 100 may include one or more electrodes 112 for sensing electrical activity of heart 106 and/or delivering electrical stimulation to heart 106. Atrial device 100 includes two electrodes 112, although more than two electrodes may be included on an atrial device in other examples. Electrode 112-1 may referred to as "tip electrode 112-1." Electrode 112-2 may be referred to as a "ring electrode 112-2." Fixation tines 110 may anchor atrial device 100 to cardiac tissue such that tip electrode 112-1 maintains contact with the cardiac tissue. Ring electrode 112-2 may be located on housing 108. For example, ring electrode 112-2 may be a cylindrical electrode that wraps around housing 108. Although ring electrode 112-2 is illustrated as a cylindrical electrode that wraps around housing 108, ring electrode 112-2 may include other geometries. In some examples, housing 108 may be formed from a conductive material. In these examples, housing 108 may act as an electrode of atrial device 100.

Housing 108 houses electronic components of atrial device 100. Electronic components may include any discrete and/or integrated electronic circuit components that implement analog and/or digital circuits capable of producing the functions attributed to atrial device 100 described herein. For example, housing 108 may house electronic components that sense electrical activity via electrodes 112 and/or deliver electrical stimulation via electrodes 112. Additionally, housing 108 may also include memory that includes instructions that, when executed by one or more processing circuits housed within housing 108, cause atrial device 100 to perform various functions attributed to atrial device 100 herein. Housing 108 may also house sensors that sense physiological conditions of patient 102, such as an accelerometer and/or a pressure sensor.

In some examples, housing 108 may house a communication module that enables leadless device 100 to communicate with other electronic devices, such as programmer 114 or other external patient monitor. In some examples, housing 108 may house an antenna for wireless communication. Housing 108 may also include a power source, such as a battery. Electronic components included within housing are described in further detail hereinafter.

Figure 2:
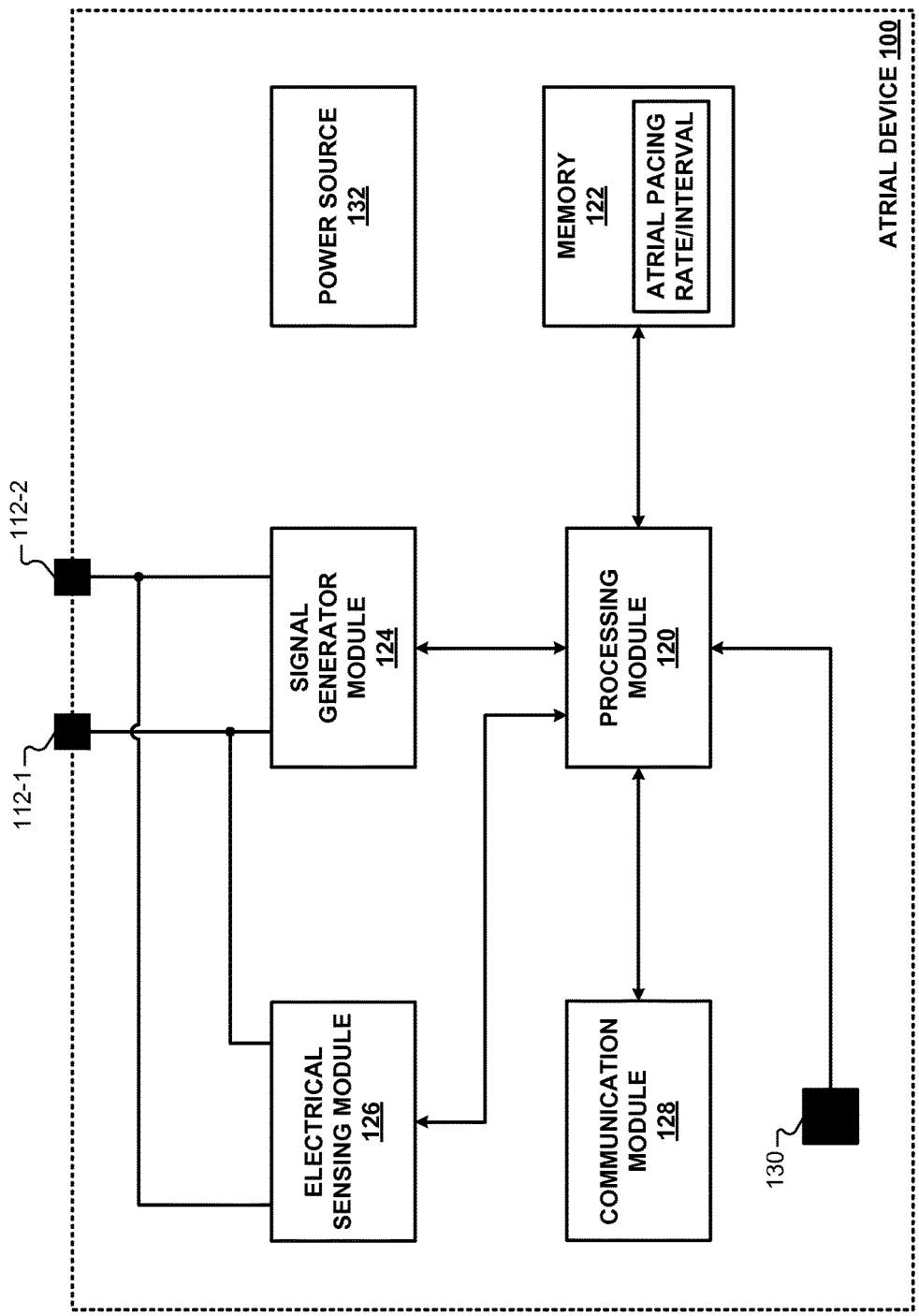
FIG. 2 is a functional block diagram of the example leadless pacemaker device.

FIG. 2 shows a functional block diagram of an example atrial device 100 configured for implantation within atrium 104 (FIG. 3). FIG. 3 shows a therapy system including atrial device 100 and programmer 114 that may be used to program atrial device 100 and retrieve data from atrial device 100. Atrial device 100 includes a processing module 120, memory 122, a signal generator module 124, an electrical sensing module 126, a communication module 128, a sensor 130, and a power source 132. Power source 132 may include a battery, e.g., a rechargeable or non-rechargeable battery.

Modules included in atrial device 100 and ventricular device 200 (FIGS. 11-12) represent functionality that may be included in atrial device 100 and ventricular device 200 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 120 may communicate with memory 122. Memory 122 may include computer-readable instructions that, when executed by processing module 120, cause processing module 120 to perform the various functions attributed to processing module 120 herein. Memory 122 may include any volatile, non-volatile, magnetic, or electrical media, such as RAM, ROM, NVRAM, EEPROM, Flash memory, or any other digital media. For example, memory 122 may include pacing instructions and values, such as the baseline atrial pacing rate, the baseline atrial pacing interval and the baseline AV interval. The pacing instructions and values may be updated by programmer 114 (FIG. 3). Pacing instructions included in memory 122 may cause atrial device 100 to operate as described herein with respect to FIGS. 4-10.

Processing module 120 may communicate with signal generator module 124 and electrical sensing module 126. Signal generator module 124 and electrical sensing module 126 are electrically coupled to electrodes 112. Electrical sensing module 126 is configured to monitor signals from electrodes 112 in order to monitor electrical activity of heart 106. Signal generator module 124 is configured to deliver electrical stimulation to atrium 104 via electrodes 112.

Processing module 120 may control signal generator module 124 to generate and deliver electrical stimulation to atrium 104 via electrodes 112. Electrical stimulation may include pacing pulses. In some examples, electrical stimulation may also include anti-tachycardia pacing (ATP) therapy. Processing module 120 may control signal generator module 124 to deliver electrical stimulation therapy according to one or more atrial therapy programs including pacing instructions and values, which may be stored in memory 122.

Electrical sensing module 126 may include circuits that acquire electrical signals. Electrical signals acquired by electrical sensing module 126 may include intrinsic cardiac electrical activity, such as intrinsic atrial and/or intrinsic ventricular cardiac electrical activity. Electrical sensing module 126 may filter, amplify, and digitize the acquired electrical signals to generate raw digital data. Processing module 120 may receive the digitized data generated by electrical sensing module 126. In some examples, processing module 120 may perform various digital signal processing operations on the raw data, such as digital filtering.

Processing module 120 may sense cardiac events based on the data received from electrical sensing module 126. For example, processing module 120 may sense atrial events based on the data received from electrical sensing module 126. In some examples, processing module 120 may sense ventricular activation based on the data received from electrical sensing module 126. For example, processing module 120 may detect FFRWs indicative of ventricular activation based on the data received from electrical sensing module 126.

Sensor 130 may comprise at least one of a variety of different sensors. For example, sensor 130 may comprise at least one of a pressure sensor and an accelerometer. Sensor 130 may generate signals that indicate at least one of an activity level of patient 102, a hemodynamic pressure, and heart sounds. Processing module 120 may detect, for example, an activity level of patient 102, a hemodynamic pressure, and heart sounds based on the signals generated by sensor 130.

Communication module 128 may include any suitable hardware (e.g., an antenna), firmware, software, or any combination thereof for communicating with another device, such as programmer 114 or a patient monitor. Under the control of processing module 120, communication module 128 may receive downlink telemetry from and send uplink telemetry to other devices, such as programmer 114 (FIG. 3) or a patient monitor, with the aid of an antenna included in communication module 128. As described herein, a leadless pacing system (e.g., leadless pacing system 202 of FIG. 11) may coordinate pacing of heart 106 based on sensed cardiac electrical and/or mechanical activity without establishment of a communication link between atrial device 100 and ventricular device 200. Accordingly, communication module 128 is not required to include functionality that provides for communication between atrial device 100 and ventricular device 200.

Programmer 114 may be a handheld computing device, desktop computing device, a networked computing device, etc. Programmer 114 may include a computer-readable storage medium having instructions that cause a processor of programmer 114 to provide the functions attributed to programmer 114 in the present disclosure. Atrial device 100 and ventricular device 200 may wirelessly communicate with programmer 114. For example, atrial device 100 and ventricular device 200 (FIG. 11) may transfer data to programmer 114 and may receive data from programmer 114. Programmer 114 may also wirelessly program and/or wirelessly charge atrial device 100 and ventricular device 200.

Data retrieved from atrial device 100 and ventricular device 200 using programmer 114 may include cardiac EGMs stored by atrial device 100 and ventricular device 200 that indicate electrical activity of heart 106 and marker channel data that indicates the occurrence and timing of sensing, diagnosis, and therapy events associated with atrial device 100 and ventricular device 100. Data transferred to atrial device 100 and ventricular device 200 using programmer 114 may include, for example, operational programs for devices 100, 200 that cause devices 100, 200 to operate as described herein.

Processing module 120 may control atrial pacing timing based on the detection of ventricular activation events in a variety of different ways. The manner in which processing module 120 controls atrial pacing timing may depend on when a ventricular activation event occurs relative to the atrial event that preceded the ventricular activation event. In other words, the manner in which processing module 120 controls atrial pacing timing may depend on when processing module detects a FFRW or an S1 heart sound relative to the atrial event that preceded the detected FFRW or the detected S1 heart sound.

FIGS. 4-10 show example ways in which processing module 120 may control atrial pacing timing based on when ventricular activation is detected during the cardiac cycle. FIG. 4 and FIGS. 6-10 include markers (e.g., lines 134 in FIG. 6) labeled "A." For purposes of explanation, unless indicated otherwise, it may be assumed that the label "A" indicates an atrial pace delivered to atrium 104.

FIG. 4 includes markers (e.g., dotted lines 136) labeled $V_{ACT}$. Marker $V_{ACT}$ indicates when processing module 120 detects a ventricular activation event. As described herein, processing module 120 may detect ventricular activation based on FFRWs and/or S1 heart sounds. FIGS. 6-10 include markers (e.g., lines 138 in FIG. 6) labeled "FF." Marker FF indicates when processing module 120 detects FFRWs.

FIG. 4 and FIG. 6 show atrial pacing timing during normal AV conduction. FIG. 4 illustrates the general concept of controlling atrial pacing based on the detection of ventricular activation. FIG. 6 shows an example in which processing module 120 detects ventricular activation by detecting FFRWs. In the example of FIG. 6, processing module 120 controls atrial pacing timing based on when FFRWs are detected during the cardiac cycle. Atrial pacing timing based on the detection of FFRWs is also described and illustrated with respect to FIGS. 7-10. Although detection of FFRWs and control of atrial pacing timing based on the detection of FFRWs is described herein with respect to FIGS. 6-10, processing module 120 may also control atrial pacing timing based on the detection of S1 heart sounds. In examples where processing module 120 controls atrial pacing timing based on S1 heart sounds, the timing diagrams may be similar to FIGS. 6-10, except the FF labels would be replaced with S1 heart sound labels indicating when S1 heart sounds were detected.

FIG. 4 shows atrial pacing timing based on the detection of ventricular activation during normal AV conduction. The $A-V_{ACT}$ interval during normal conduction timing may have a value of T1 seconds. Processing module 120 may control atrial pacing timing based on the value of the $A-V_{ACT}$ interval (i.e., T1). As illustrated, processing module 120 may set the subsequent pacing pulse to occur T2 seconds after ventricular activation is detected during normal AV conduction.

During normal AV conduction, the $A-V_{ACT}$ interval may be characterized as having a normal duration. In other words, T1 may represent the normal amount of time between an atrial event and ventricular activation during normal AV conduction. Processing module 120 may control stimulation generator module 124 to deliver pacing pulses at the baseline atrial pacing rate (e.g., 60 bpm) such that the intervals between atrial events are approximately equal to the baseline atrial pacing interval. As described herein, the baseline atrial pacing rate (i.e., the reciprocal of the baseline atrial pacing interval) may be a value maintained by atrial device 100 based on one or more of a variety of different factors, such as the activity level of patient 102. With respect to FIGS. 4-10, the baseline atrial pacing interval may be approximately T3 seconds.

In examples where processing module 120 determines that the $A-V_{ACT}$ interval is normal (e.g., approximately equal to T1), processing module 120 may schedule the next pace to occur approximately T2 seconds after the detected ventricular activation. Processing module 120 may determine the value of T2 based on the baseline atrial pacing interval and the magnitude of the $A-V_{ACT}$ interval. In examples where processing module 120 determines the $A-V_{ACT}$ interval has a normal duration (e.g., approximately T1), processing module 120 may set the next pacing pulse to occur at a time that maintains the baseline atrial pacing interval. In other words, when processing module 120 determines that the $A-V_{ACT}$ interval is approximately equal to T1, processing module 120 may set the next pacing pulse to occur approximately T2 seconds after the detection of ventricular activation. The sum of intervals T1 and T2 may be approximately T3. In this manner, during normal AV conduction over a plurality of cardiac cycles, processing module 120 may control stimulation generator module 124 to deliver pacing pulses such that the baseline atrial pacing rate is maintained over the plurality of cardiac cycles.

Processing module 120 may control atrial pacing timing in different ways depending on the duration of the $A-V_{ACT}$ interval. Although operation of processing module 120 is described above in examples where $A-V_{ACT}$ has a normal duration T1, $A-V_{ACT}$ may have a short duration (e.g., less than T1) or a long duration (e.g., greater than T1). Processing module 120 may control atrial pacing timing differently based on which $A-V_{ACT}$ duration is detected.

Figure 5:
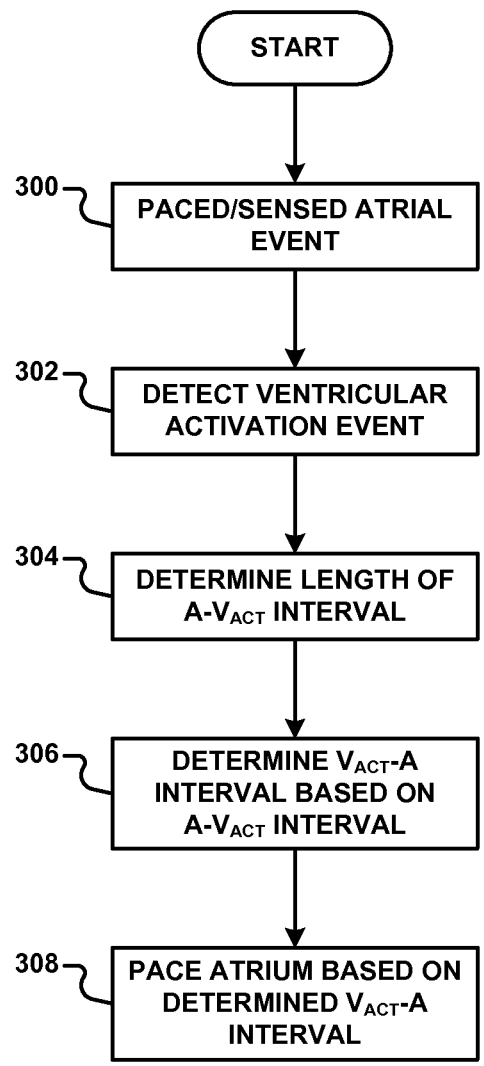
FIG. 5 is a flowchart of a method for controlling atrial pacing timing based on detection of ventricular activation.

FIG. 5 is a flowchart that illustrates an example method for controlling atrial pacing timing. It may be assumed that the start of the method of FIG. 5 occurs just prior to an atrial event (paced or sensed). Initially, an atrial event occurs in block (300). In some examples, the atrial event may be a paced atrial event that is initiated by stimulation generator module 124 under control of processing module 120. In other examples, the atrial event that occurs in block (300) may be an intrinsic atrial event that is detected by processing module 120, e.g., via sensing module 122. The atrial event of block (300) precedes (e.g., precipitates) a ventricular activation event. Processing module 120 may detect the ventricular activation event in block (302). In some examples, processing module 120 may detect the ventricular activation event based on the detection of a FFRW in block (302). In some examples, processing module 120 may detect the ventricular activation event based on the detection of an S1 heart sound in block (302).

Processing module 120 may then determine the length of the $A-V_{ACT}$ interval (304). In examples where processing module 120 detects ventricular activation based on the detection of a FFRW, the interval of time between the atrial event of block (300) and the FFRW detected in block (302) may be referred to as the A-FF interval. In examples where processing module 120 detects ventricular activation based on the detection of an S1 heart sound, the interval of time between the atrial event of block (300) and the S1 heart sound detected in block (302) may be referred to as the A-S1 interval.

Processing module 120 may then determine when to deliver (i.e., schedule) a pacing pulse based on the length of the A-V$_{ACT}$ interval (306). Put another way, processing module 120 may determine the V$_{ACT}$-A interval based on the length of the A-V$_{ACT}$ interval. In general, the length of the A-V$_{ACT}$ interval may be characterized as normal, short, or long. Processing module 120 may determine when to deliver a pacing pulse based on which of the A-V$_{ACT}$ intervals are detected. As described above, when AV conduction is normal (e.g., the A-V$_{ACT}$ interval is approximately T1), processing module 120 may set the next pacing pulse to occur T2 seconds after the detected ventricular activation event such that the interval between atrial events is approximately equal to the baseline atrial pacing interval T3.

In some examples, the A-V$_{ACT}$ interval may not be approximately equal to T1, but instead, the A-V$_{ACT}$ interval may be shorter than T1 or longer than T1. In examples where processing module 120 determines that the A-V$_{ACT}$ interval is longer than T1 (e.g., by a threshold amount of time), processing module 120 may identify the A-V$_{ACT}$ interval as a long A-V$_{ACT}$ interval. In examples where processing module 120 identifies the A-V$_{ACT}$ interval is a long interval, processing module 120 may control atrial pacing timing in a manner that is different than that described above in the scenario in which the A-V$_{ACT}$ interval is a normal interval. Example control of atrial pacing timing when a long interval is detected is described herein with reference to FIGS. 8A-8B.

In examples where processing module 120 determines that the A-V$_{ACT}$ interval is shorter than T1 (e.g., by a threshold amount of time), processing module 120 may identify the A-V$_{ACT}$ interval as a short A-V$_{ACT}$ interval. In examples where processing module 120 identifies the A-V$_{ACT}$ interval as a short interval, processing module 120 may control pacing timing in a manner that is different than that described above in the scenario in which the A-V$_{ACT}$ interval is a normal interval. Example control of atrial pacing timing when a short interval is detected is described herein with reference to FIGS. 7A-7B.

After scheduling the pacing pulse, processing module 120 may control stimulation generator module 124 to deliver the pacing pulse at the scheduled time (308). In some examples, processing module 120 may inhibit pacing when an intrinsic atrial event is detected prior to the scheduled pacing time. Although processing module 120 may inhibit pacing when an intrinsic atrial event is detected prior to the scheduled pacing time, such inhibition of pacing is not illustrated in FIG. 4 and FIGS. 6-10. Instead, FIG. 4 and FIGS. 6-10 illustrate the delivery of pacing pulses during each cardiac cycle in order to illustrate how atrial pacing timing is scheduled based on when ventricular activation is detected during a cardiac cycle.

As described above, ventricular activation may refer to electrical depolarization of the ventricular cardiac tissue and the subsequent mechanical contraction of the ventricular cardiac tissue. In one example, processing module 120 may detect ventricular activation by detecting FFRWs. Put another way, detection of FFRWs is one example of detecting ventricular activation. Similarly, processing module 120 may detect ventricular activation by detecting S1 heart sounds. Atrial device 100 is described hereinafter as detecting FFRWs and controlling atrial pacing timing based on the detection of FFRWs. Although FIGS. 6-10 describe atrial pacing timing based on the detection of FFRWs, it is contemplated that atrial device 100 may control atrial pacing timing based on S1 heart sounds in a similar manner. For example, the detection of S1 heart sounds may generally be substituted for the detection of FFRWs in FIGS. 6-10.

FIG. 6 shows atrial pacing timing based on the detection of FFRWs when AV conduction is normal. During normal AV conduction, processing module 120 may control pacing timing in a similar manner as described above with respect to FIGS. 4-5. For example, during normal AV conduction, the A-FF interval may be approximately T1, and processing module 120 may set the FF-A interval equal to approximately T2 so that the interval between atrial events may be approximately equal to the baseline atrial pacing interval T3. In some examples, normal AV conduction may persist for a period of time. While AV conduction persists, processing module 120 may continue to control atrial pacing timing according to FIG. 6.

Although normal A-FF intervals of FIG. 6 may persist for a period of time, in some examples, the duration of A-FF intervals may deviate from the normal A-FF interval T1. In some examples, processing module 120 may detect a short A-FF interval. In general, a short A-FF interval may be an interval that is shorter than the normal A-FF interval, e.g., by a threshold amount of time. Processing module 120 may identify the A-FF interval as a short interval when the A-FF interval is less than the normal A-FF interval by a threshold amount of time.

Processing module 120 may control atrial pacing timing in a variety of different ways when processing module detects a short A-FF interval. In some examples, processing module 120 may control atrial pacing timing in order to maintain a normal FF-FF interval (i.e., a normal V-V interval). Control of atrial pacing timing to maintain a normal FF-FF interval is illustrated in FIG. 7A. In other examples, processing module 120 may control atrial pacing timing to maintain a normal A-A interval (e.g., a baseline atrial pacing interval). Control of atrial pacing timing to maintain a normal A-A interval is illustrated in FIG. 7B.

Figure 7B:
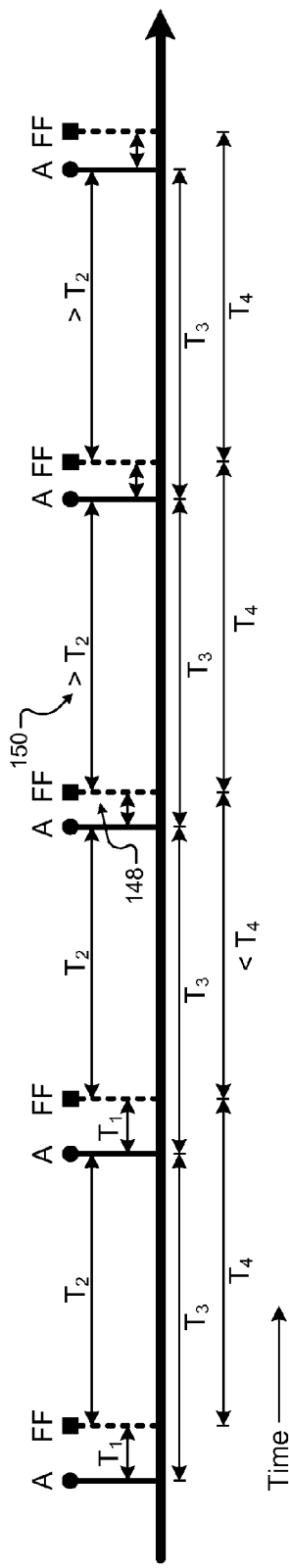

Two different responses of processing module 120 in response to a detected short A-FF interval are illustrated in FIGS. 7A-7B. FIG. 7A shows a scenario in which normal atrial pacing timing is maintained until processing module 120 detects a short A-FF interval at 140. In FIG. 7A, processing module 120 schedules the pacing pulse to occur approximately T2 seconds after detection of the FFRW in response to a determination that the A-FF interval is a short A-FF interval. Put another way, processing module 120 sets the subsequent pacing pulse to occur such that a normal FF-A interval (i.e., T2) is obtained. By setting the pacing pulse to occur approximately T2 seconds after the detected FFRW, processing module 120 may maintain the normal FF-FF interval (i.e., V-V interval) assuming that the subsequent A-FF interval returns to normal (i.e., T1). In FIG. 7A, the normal A-FF interval T1 returns at 142 subsequent to the single cardiac cycle including the shortened A-FF interval. Accordingly, in the example of FIG. 7A, the FF-FF interval 144 returns to normal (i.e., approximately T4) during the cardiac cycle that is subsequent to the cardiac cycle including the short A-FF interval.

As indicated at 146, pacing according to FIG. 7A causes the A-A interval to shorten (e.g., to a value less than T3) because the sum of the normal FF-A interval (T2) and the shortened A-FF interval 140 is less than T3. It follows then that pacing according to the strategy of FIG. 7A for an extended period of time (i.e., a plurality of cardiac cycles) may cause an increase in the atrial pacing rate to a rate that is greater than the desired baseline atrial pacing rate. FIG. 7B shows control of atrial pacing timing to maintain the A-A interval at the baseline atrial pacing interval in the scenario where the shortened A-FF intervals are persistent for an extended period of time.

FIG. 7B shows a scenario in which normal atrial pacing timing is maintained until processing module 120 detects a short A-FF interval at 148. In FIG. 7B, shortened A-FF intervals are persistent for a plurality of cardiac cycles after detection of the first short A-FF interval at 148. In FIG. 7B, processing module 120 controls atrial pacing timing to maintain a normal A-A interval having a duration of T3. Processing module 120 maintains normal A-A intervals by extending the FF-A interval to a value that is greater than the normal FF-A interval of T2, as indicated at 150. Put another way, upon detecting a short A-FF interval, processing module 120 may extend the FF-A interval to a value that is greater than the normal FF-A value in order to maintain the A-A interval at the normal duration of T3. In order to maintain the A-A interval at the normal duration of T3, processing module 120 may determine how much shorter the shortened A-FF interval 148 is than the normal interval T1, then add the difference between the normal and shortened A-FF intervals to the normal FF-A interval T2.

As described above, in some examples, short A-FF intervals may be a temporary in that only one or a few short A-FF intervals occur. However, in other examples, the short A-FF intervals may persist for a period of time. In some examples, processing module 120 may be configured to control atrial pacing timing under the initial assumption that the initial short A-FF interval is temporary. For example, processing module 120 may be configured to initially respond to a shortened A-FF interval by controlling atrial pacing timing in the manner described in FIG. 7A. Processing module 120 may be further configured such that if short A-FF intervals persist, processing module 120 may control atrial pacing timing to maintain a normal A-A interval, as described with respect to FIG. 7B. In this example, processing module 120 may transition from controlling atrial pacing according to FIG. 7A to controlling atrial pacing according to FIG. 7B upon detection of a threshold number of short A-FF intervals. In this manner, processing module 120 may initially control pacing to maintain the FF-FF interval, but then control pacing in order to maintain the atrial pacing rate at the baseline atrial pacing rate when the short A-FF intervals are a long term condition. Upon detection of a normal A-FF interval T1, processing module 120 may return to pacing according to FIG. 6.

Referring now to FIGS. 8A-8B, in some examples, processing module 120 may detect a long A-FF interval. In general, a long A-FF interval may be an interval that is longer than the normal A-FF interval, e.g., by a threshold amount of time. Processing module 120 may identify the A-FF interval is a long A-FF interval when the A-FF interval is greater than the normal A-FF interval by a threshold amount of time.

Processing module 120 may control atrial pacing timing in a variety of different ways when processing module 120 detects a long A-FF interval. In some examples, processing module 120 may control atrial pacing timing in order to maintain a normal FF-FF interval (i.e., a normal V-V interval). Control of atrial pacing timing to maintain a normal FF-FF interval after a long A-FF interval is detected is illustrated in FIG. 8A. In other examples, processing module 120 may control atrial pacing timing to maintain a normal A-A interval. Control of atrial pacing timing to maintain a normal A-A interval after detection of a long A-FF interval is illustrated in FIG. 8B.

Two different responses of processing module 120 in response to detection of a long A-FF interval are illustrated in FIGS. 8A-8B. FIG. 8A shows a scenario in which normal atrial pacing timing is maintained until processing module 120 detects a long A-FF interval at 152. In FIG. 8A, processing module 120 schedules the pacing pulse to occur approximately T2 seconds after detection of the FFRW in response to a determination that the A-FF interval is a long A-FF interval at 152. Put another way, processing module 120 sets the subsequent pacing pulse to occur such that a normal FF-A interval (i.e., T2) is obtained. By setting the pacing pulse to occur approximately T2 seconds after the detected FFRW, processing module 120 may maintain the normal FF-FF interval in the next cardiac cycle assuming that the subsequent A-FF interval returns to normal (i.e., T1). In FIG. 8A, the normal A-FF interval T1 returns at 154 subsequent to the single cardiac cycle including the long A-FF interval. Accordingly, as illustrated at 156 in the example of FIG. 8A, the FF-FF interval returns to normal (i.e., approximately T4) during the cardiac cycle that is subsequent to the cardiac cycle including the long A-FF interval.

As illustrated at 158, pacing according to FIG. 8A causes the A-A interval to lengthen (e.g., to a value greater than T3) because the sum of the lengthened FF-A interval and the normal FF-A interval (T2) is greater than T3. It follows then that pacing according to the strategy of FIG. 8A may cause a decrease in the atrial pacing rate, at least for a single cardiac cycle. FIG. 8B shows control of atrial pacing timing to maintain the A-A interval at the baseline atrial pacing interval in the scenario where long A-FF intervals are persistent for an extended period of time.

FIG. 8B shows a scenario in which normal atrial pacing timing is maintained until processing module 120 detects a long A-FF interval at 160. In FIG. 8B, long A-FF intervals are persistent for a plurality of cardiac cycles after detection of the first long A-FF interval at 160. In FIG. 8B, processing module 120 controls atrial pacing timing to maintain a normal A-A interval having a duration of T3. Processing module 120 maintains normal A-A intervals by shortening the FF-A interval to a value that is less than the normal FF-A interval of T2, as illustrated at 162. Put another way, upon detecting a long A-FF interval, processing module 120 may shorten the FF-A interval to a value that is less than the normal FF-A value in order to maintain the A-A interval at the normal duration of T3. In order to maintain the A-A interval at the normal duration of T3, processing module 120 may determine how much longer the long A-FF interval 162 is than the normal interval T1, then subtract the difference between the normal and long A-FF intervals from the normal FF-A interval T2.

As described above, in some examples, long A-FF intervals may be temporary such that only one or a few consecutive long A-FF intervals occur. However, in other examples, the long A-FF intervals may persist for a period of time. In some examples, processing module 120 may be configured to control atrial pacing timing under the initial assumption that the initial long A-FF interval is temporary. For example, processing module 120 may be configured to initially respond to a long A-FF interval by controlling atrial pacing timing in the manner described in FIG. 8A. Processing module 120 may be further configured such that if long A-FF intervals persist, processing module 120 may control atrial pacing timing to maintain a normal A-A interval, as described with respect to FIG. 8B. In this example, processing module 120 may transition from controlling atrial pacing according to FIG. 8A to controlling atrial pacing according to FIG. 8B upon detection of a threshold number of long A-FF intervals. In this manner, processing module 120 may initially control pacing to maintain the FF-FF interval, but then control pacing in order to maintain the atrial pacing rate at or near the baseline atrial pacing rate when the long A-FF intervals are a long term condition. Upon detection of a normal A-FF interval (i.e., T1) after detection of one or more long A-FF intervals, processing module 120 may return to pacing according to FIG. 6.

Processing module 120 may control atrial pacing timing according to FIGS. 8A-8B subject to some constraints. For example, processing module 120 may be configured to maintain the A-A pacing interval at a value that is less than a maximum A-A interval (i.e., a minimum atrial pacing rate). Accordingly, in some examples, processing module 120 may be configured to set a pacing pulse such that the A-A interval is less than a maximum A-A interval. The minimum atrial pacing rate (maximum A-A interval) may be stored in memory 122 in some examples.

Figure 9:
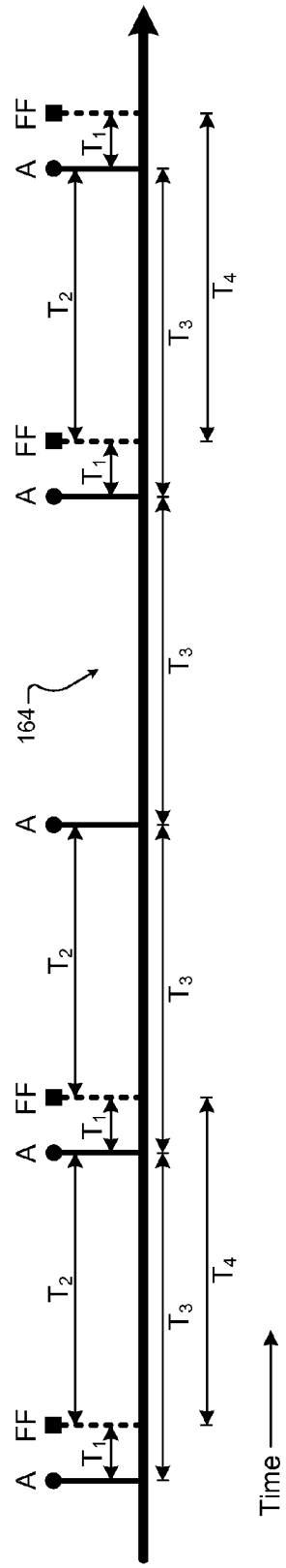
FIG. 9 is an example atrial pacing timing diagram including an interval in which a far-field R-wave is undetected.

FIG. 9 shows example atrial pacing timing in the case that a FFRW goes undetected by processing module 120 or did not occur due to AV block, as illustrated at 164. Processing module 120 may be configured to pace at the baseline atrial pacing rate when a FFRW is not detected after an atrial event. Processing module 120 may determine whether a FFRW is absent after an atrial event based on the amount of time that has passed since the atrial event. For example, if a threshold amount of time has passed after an atrial event without detection of a FFRW, processing module 120 may determine that a FFRW went undetected during the cardiac cycle. Accordingly, if processing module 120 does not detect a FFRW event within a threshold amount of time (e.g., within 400 ms), processing module 120 may schedule a pacing pulse to occur T3 seconds after the last detected atrial event.

Figure 10:
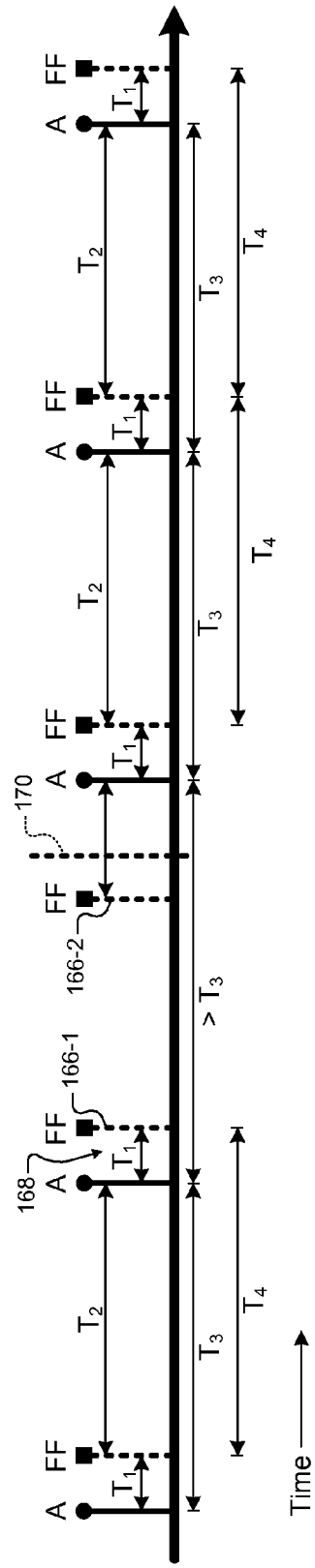
FIG. 10 is an example atrial pacing timing diagram including an interval in which multiple far-field R-waves are detected between atrial events.

FIG. 10 shows example atrial pacing timing in the case that processing module 120 detects multiple FFRWs after an atrial event. In this example, processing module 120 may detect a first FFRW 166-1 and schedule atrial pacing timing based on the first detected FFRW 166-1. For example, processing module 120 may schedule a pacing pulse to occur based on the length of the A-FF interval at 168. In some examples, processing module 120 may set the pacing pulse based on whether A-FF interval is normal, short, or long, as described above with respect to FIGS. 7A-8B. The pacing pulse scheduled based on the A-FF interval at 168 is illustrated by the dotted line 170. In cases where processing module 120 schedules a pacing pulse based on a first detected FFRW but detects a second FFRW 166-2 prior to delivery of the scheduled pacing pulse, processing module 120 may determine that multiple FFRWs are detected.

Upon detecting multiple FFRWs, processing module 120 may control pacing timing to prevent pacing such that the atrial contraction occurs against a closed AV valve. For example, upon detection of multiple FFRWs subsequent to a single atrial event, processing module 120 may delay atrial pacing for a period of time to prevent pacing the atrium against a closed valve. In some examples, processing module 120 may delay atrial pacing for T2 seconds after the last detected FFRW. In examples where pacing T2 seconds after the last detected FFRW would cause the atrial pacing rate to drop below a minimum atrial pacing rate, processing module 120 may pace the atrium such that the minimum atrial pacing rate is not violated.

With respect to FIG. 10, processing module 120 may detect a first FFRW at 166-1. In the example of FIG. 10, the A-FF interval is approximately equal to T1. Accordingly, as described above, processing module 120 may set an initial pacing pulse to occur approximately T2 seconds after first FFRW 166-1. The initial scheduled pacing pulse is illustrated as dotted line 170. Prior to delivering the initially scheduled pacing pulse 170, processing module 120 detects a second FFRW 166-2. Upon detection of the second FFRW 166-2, processing module 120 may update the time at which the pacing pulse is to be delivered. For example, processing module 120 may update the pacing pulse to occur a period of time after the second FFRW 166-2 that will likely prevent pacing the atrium while the valve is closed.

Figure 11:
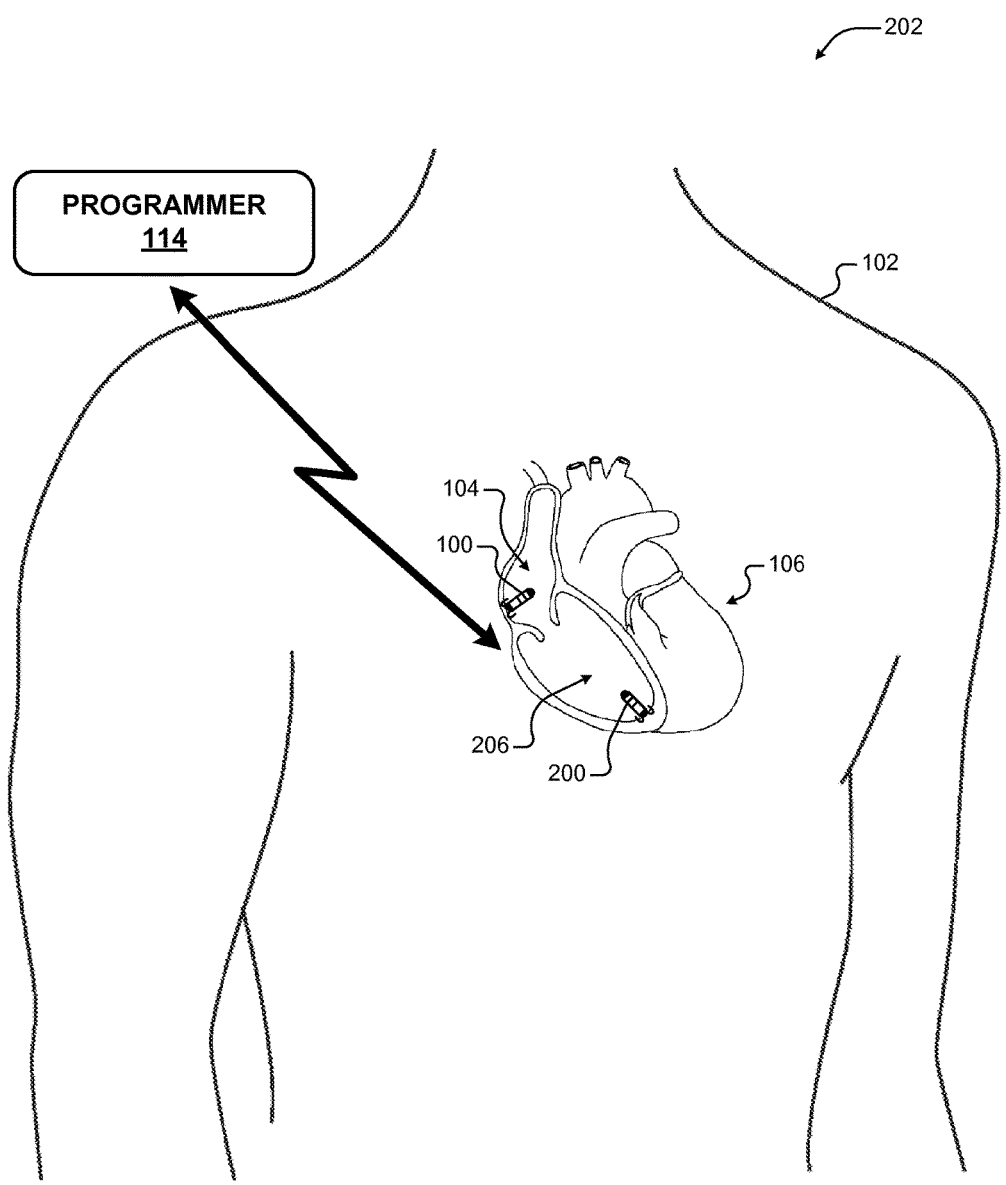
FIG. 11 shows an example leadless pacing system including an atrial pacemaker device and a ventricular pacemaker device.

FIG. 11 shows an example leadless pacing system 202. Leadless pacing system 202 includes atrial device 100 and a leadless ventricular pacemaker device 200 (hereinafter "ventricular device 200"). Ventricular device 200 may be configured to pace the ventricle, sense intrinsic ventricular depolarizations, and inhibit ventricular pacing in response to detected ventricular depolarization. The structure of ventricular device 200 may be similar to the structure of atrial device 100. For example, ventricular device 200 may have a housing, fixation tines, and electrodes that are similar to housing 108, fixation tines 110, and electrodes 112 of atrial device 100 (FIG. 1).

The fixation tines of ventricular device 200 are configured to connect (e.g., anchor) ventricular device 200 to heart 106. For example, the fixation tines of ventricular device 200 may be configured to anchor ventricular device 200 within the right or left ventricle. As illustrated and described herein with respect to FIG. 11, ventricular device 200 may be implanted within right ventricle 206.

Ventricular device 200 may include two or more electrodes (e.g., electrodes 222-1, 222-2 of FIG. 12) for sensing electrical activity of heart 106 and/or delivering electrical stimulation to heart 106. Ventricular device 200 may include a tip electrode and a ring electrode, similar to tip electrode 112-1 and ring electrode 112-2 of atrial device 100 (FIG. 1). The fixation tines of ventricular device 200 may anchor ventricular device 200 to cardiac tissue such that the tip electrode of ventricular device 200 maintains contact with the cardiac tissue.

Ventricular device 200 may include a housing that is similar to housing 108 of atrial device 100. The housing of ventricular device 200 houses electronic components of ventricular device 200. Electronic components may include any discrete and/or integrated electronic circuit components that implement analog and/or digital circuits capable of producing the functions attributed to ventricular device 200 described herein. For example, the housing of ventricular device may house electronic components that sense electrical activity via the electrodes of ventricular device 200 and/or deliver electrical stimulation via the electrodes of ventricular device 200. The housing of ventricular device may also include memory that includes instructions that, when executed by one or more processing circuits housed within the housing of ventricular device 200, cause ventricular device 200 to perform various functions attributed to ventricular device 200 herein. Ventricular device 200 may also include sensors that sense physiological conditions of patient 102, such as an accelerometer and/or a pressure sensor.

In some examples, ventricular device 200 may include a communication module that enables ventricular device 200 to communicate with other electronic devices, such as programmer 114. In some examples, ventricular device 200 may include an antenna for wireless communication with other devices. Ventricular device 200 may also include a power source, such as a battery.

Figure 12:
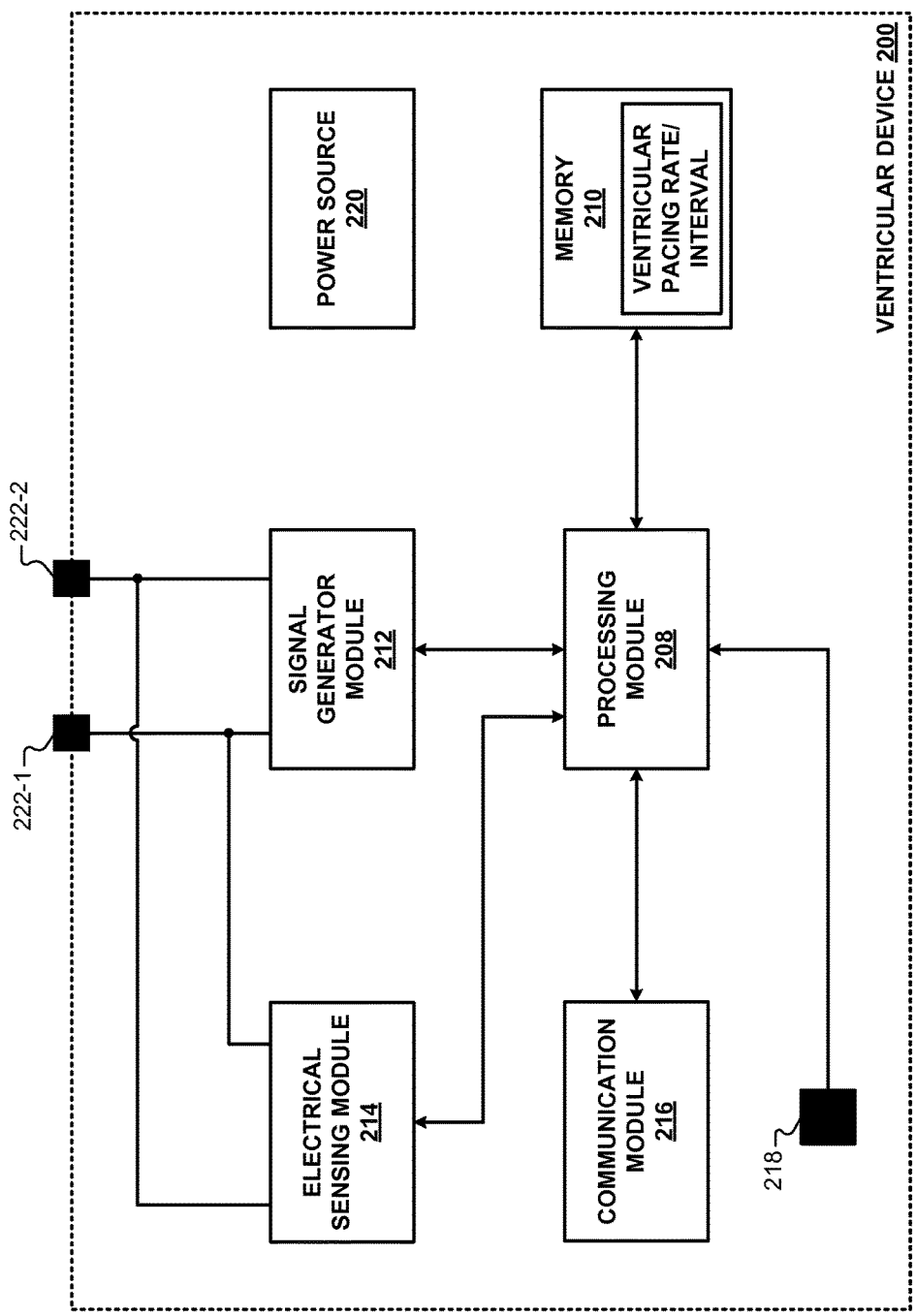
FIG. 12 is a functional block diagram of the example ventricular device.

FIG. 12 shows a functional block diagram of an example ventricular device 200 configured for implantation within ventricle 206. Ventricular device 200 includes a processing module 208, memory 210, a signal generator module 212, an electrical sensing module 214, a communication module 216, a sensor 218, and a power source 220. Power source 220 may include a battery, e.g., a rechargeable or non-rechargeable battery.

Processing module 208 may communicate with memory 210. Memory 210 may include computer-readable instructions that, when executed by processing module 208, cause processing module 208 to perform the various functions attributed to processing module 208 herein. Memory 210 may include any volatile, non-volatile, magnetic, or electrical media, such as RAM, ROM, NVRAM, EEPROM, Flash memory, or any other digital media. For example, memory 210 may include ventricular pacing instructions and values, such as a ventricular pacing rate, which may be updated by programmer 114. Ventricular pacing instructions included in memory 114 may cause ventricular device 200 to operate as described herein.

Processing module 208 may communicate with signal generator module 212 and electrical sensing module 214. Signal generator module 212 and electrical sensing module 214 are electrically coupled to electrodes 222-1, 222-2 (collectively "electrodes 222"). Electrical sensing module 214 is configured to monitor signals from electrodes 222 in order to monitor electrical activity of heart 106. Signal generator module 212 is configured to deliver electrical stimulation to heart 106 via electrodes 222. Processing module 208 may control signal generator module 212 to generate and deliver electrical stimulation to ventricle 206 via electrodes 222. Electrical stimulation may include pacing pulses. Processing module 208 may control signal generator module 136 to deliver electrical stimulation therapy according to one or more ventricular therapy programs that define a ventricular pacing rate. The ventricular therapy programs may be stored in memory 210.

Electrical sensing module 214 may include circuits that acquire electrical signals. Electrical signals acquired by electrical sensing module 214 may include intrinsic cardiac electrical activity, such as intrinsic ventricular depolarizations. Electrical sensing module 214 may filter, amplify, and digitize the acquired electrical signals to generate raw digital data. Processing module 208 may receive the digitized data generated by electrical sensing module 214. In some examples, processing module 208 may perform various digital signal processing operations on the raw data, such as digital filtering. Processing module 208 may sense ventricular events (e.g., intrinsic ventricular depolarizations) based on the data received from electrical sensing module 214.

Sensor 218 may comprise at least one of a variety of different sensors. For example, sensor 218 may comprise at least one of a pressure sensor and an accelerometer. Sensor 218 may generate signals that indicate an activity level of patient 102. Processing module 208 may detect an activity level of patient 102 based on the signals generated by sensor 218.

Communication module 216 may include any suitable hardware (e.g., an antenna), firmware, software, or any combination thereof for communicating with another device, such as programmer 114 or a patient monitor. Under the control of processing module 208, communication module 216 may receive downlink telemetry from and send uplink telemetry to other devices, such as programmer 114 or a patient monitor, with the aid of an antenna included in communication module 216. As described herein, a leadless pacing system (e.g., leadless pacing system 202 of FIG. 11) may coordinate pacing of heart 106 based on sensed cardiac electrical and/or mechanical activity without establishment of a communication link between atrial device 100 and ventricular device 200. Accordingly, communication module 216 is not required to include functionality that provides for communication between atrial device 100 and ventricular device 200.

Ventricular device 200 may wirelessly communicate with programmer 114. For example, ventricular device 200 may transfer data to programmer 114 and may receive data from programmer 114. Programmer 114 may also wirelessly program ventricular device 200. For example, programmer 114 may wirelessly program operational parameters of ventricular device 200, such as the ventricular pacing rate.

In general, ventricular device 200 may be configured to pace ventricle 206 at a ventricular pacing rate. In the case where ventricular device 200 detects an intrinsic ventricular depolarization prior to delivering the pacing stimulus according to the ventricular pacing rate, ventricular device 200 may withhold stimulation. The ventricular pacing rate may be set such that ventricular device 200 tends to pace ventricle 206 in situations in which AV conduction is blocked. In other words, the ventricular pacing rate may be set at a rate that provides backup pacing to ensure that ventricle 206 is paced in situations where intrinsic ventricular depolarizations do not arise as a result of atrial depolarizations. In some examples, the ventricular pacing rate may be a rate that is less than or equal to the atrial pacing rate. For example, the ventricular pacing rate may be set to 10-20 paces per minute less than the atrial rate (e.g., approximately 40 ppm). The ventricular pacing rate may also be expressed as a ventricular pacing interval. The ventricular pacing interval may be the reciprocal value of the ventricular pacing rate. Operation of ventricular device 200 with respect to FIG. 12 is now described.

Memory 210 may store the ventricular pacing rate and/or the ventricular pacing interval. In some examples, the ventricular pacing rate may initially be programmed into memory 210 upon initial implantation of ventricular device 200. The ventricular pacing rate may be updated in some examples. For example, a clinician may use programmer 114 to update the ventricular pacing rate. In some examples, processing module 208 may automatically update the ventricular pacing rate. For example, processing module 208 may determine an activity level of patient 102 and modify the ventricular pacing rate based on the activity level of patient 102. In this example, processing module 208 may increase the ventricular pacing rate upon determining that the patient activity level has increased. Processing module 208 may decrease the ventricular pacing rate upon determining that the patient activity level has decreased.

Processing module 208 may control signal generator module 212 to deliver pacing pulses at the ventricular pacing rate stored in memory 210. Processing module 208 may also inhibit the delivery of pacing pulses to ventricle 206 when processing module 208 detects an intrinsic ventricular depolarization. Accordingly, after a paced or sensed ventricular event, processing module 208 may schedule the next ventricular pacing pulse to occur such that the amount of time between the scheduled pacing pulse and the previous ventricular event is equal to the ventricular pacing interval.

As described above, the ventricular pacing rate may be set to a value that is less than the atrial pacing rate. In examples where the ventricular pacing rate is less than the atrial pacing rate and normal AV conduction is present in heart 106, ventricular device 200 may typically not pace ventricle 200. Instead, the pacing pulses delivered by atrial device 100 may cause intrinsic ventricular depolarizations that in turn cause ventricular device 200 to inhibit a scheduled ventricular pacing pulse. Accordingly, in the absence of AV block in heart 106, ventricular activation (e.g., FFRWs and S1 heart sounds) detected by atrial device 100 may typically arise due to intrinsic ventricular depolarizations.

Ventricular device 200 may pace ventricle 206 when AV block is present in heart 106. In some examples, AV block may be present temporarily in heart 106, e.g., for one or a few cardiac cycles. In other examples, AV block may persist for longer periods of time, or may be permanent. In examples where AV block occurs, the ventricular activation events (e.g., FFRWs and S1 heart sounds) detected by atrial device 100 may arise from paced ventricular events. In examples where AV block occurs temporarily between periods of AV conduction, the ventricular activations detected by atrial device 100 may arise from paced ventricular events during periods of AV block and may arise due to intrinsic ventricular depolarizations during periods of AV conduction. Accordingly, in one sense, the ventricular pacing rate of ventricular device 200 may be thought of as a backup pacing rate that causes ventricular device 200 to pace in circumstances where AV block occurs.

FIG. 8A may illustrate an example of how ventricular device 200 may provide backup ventricular pacing during AV block. With respect to FIG. 8A, if it is assumed that AV block is present during the atrial event at 224, it may be assumed that the FF event (226) detected by atrial device 100 arose due to a paced ventricular event instead of an intrinsic ventricular depolarization. In this case, the long A-FF interval at 152 would be due to the lower ventricular pacing rate (i.e., lower than the atrial pacing rate) implemented by ventricular device 200. As described above, ventricular device 200 would provide a pacing pulse to the ventricle at the expiration of the ventricular pacing interval since ventricular device 200 would not have been inhibited from pacing by a detected intrinsic ventricular depolarization.

Although processing module 120 may control atrial pacing timing based on the length of the A-$V_{ACT}$ interval (e.g., the A-FF interval), processing module 120 may also control atrial pacing timing based on other measured intervals in some examples. For example, processing module 120 may control atrial pacing timing based on the amount of time between two consecutive $V_{ACT}$ events (e.g., two consecutive FF events). In this example, processing module 120 may first determine the length of the $V_{ACT}$-$V_{ACT}$ interval (e.g., FF-FF interval), and then schedule an atrial pace based on the length of the $V_{ACT}$-$V_{ACT}$ interval. Although processing module 120 may control atrial pacing timing based on A-$V_{ACT}$ and $V_{ACT}$-$V_{ACT}$ intervals, it is contemplated that processing module 120 may additionally or alternatively control atrial pacing timing based on other measured intervals, such as A-A intervals. Control of atrial pacing timing based on the duration of the $V_{ACT}$-$V_{ACT}$ interval is described hereinafter assuming that processing module 120 detects FFRWs.

Processing module 120 may control atrial pacing timing in different ways depending on the duration of the FF-FF interval. In some examples, processing module 120 may detect a short FF-FF interval. In general, a short FF-FF interval may be an interval that is shorter than the normal FF-FF interval, e.g., by a threshold amount of time. Processing module 120 may identify the FF-FF interval as a short interval when processing module 120 determines that the FF-FF interval is less than the normal FF-FF interval by a threshold amount of time.

Processing module 120 may control atrial pacing timing in a variety of different ways when processing module 120 detects a short FF-FF interval. In some examples where processing module 120 detects a short FF-FF interval, processing module 120 may maintain the normal FF-A interval timing (e.g., T2) such that the normal FF-FF interval will be maintained during the subsequent cardiac cycle, assuming the A-FF interval of the subsequent cycle returns to the normal duration of T1. FIG. 7A shows an example in which processing module 120 may detect a shortened FF-FF interval and maintains the FF-A interval such that the subsequent FF-FF interval is maintained at the normal duration. In other examples, with respect to FIG. 7B, processing module 120 may lengthen the FF-A interval (e.g., to a value of greater than T2) in order to maintain the baseline atrial pacing interval T3 during subsequent cardiac cycles such that the patient's heart rate is maintained at the baseline atrial pacing rate.

In some examples, processing module 120 may detect a long FF-FF interval. In general, a long FF-FF interval may be an interval that is longer than the normal FF-FF interval, e.g., by a threshold amount of time. Processing module 120 may identify the FF-FF interval as a long FF-FF interval when processing module 120 determines that the FF-FF interval is greater than the normal FF-FF interval by a threshold amount of time.

With respect to FIGS. 8A-8B, processing module 120 may control atrial pacing timing in a variety of different ways when processing module 120 detects a long FF-FF interval. In some examples where processing module 120 detects a long FF-FF interval (e.g., greater than T4), processing module 120 may maintain the normal FF-A interval timing (e.g., T2) such that the FF-FF interval will be maintained at the normal duration during the subsequent cardiac cycle, assuming the A-FF interval of the subsequent cardiac cycle returns to the normal A-FF interval length. FIG. 8A shows an example in which processing module 120 may detect a long FF-FF interval and maintain the FF-A interval such that the subsequent FF-FF interval is maintained at the normal duration. In some examples, as illustrated in FIG. 8B, processing module 120 may shorten the FF-A intervals (e.g., to a value less than T2) in order to maintain the baseline atrial pacing interval during subsequent cardiac cycles.

Various examples have been described. These and other examples are within the scope of the following claims.

What is claimed is:

1. A system comprising:
   a ventricular pacing device configured for implantation entirely within a ventricle of a heart, the ventricular pacing device configured to sense intrinsic ventricular depolarizations and one of:
      inhibit delivery of pacing pulses responsive to sensed intrinsic ventricular depolarizations; or
      deliver pacing pulses to the ventricle responsive to an absence of sensed intrinsic ventricular depolarizations; and
   an atrial pacing device configured for implantation entirely within an atrium of the heart, the atrial pacing device being operable without receiving communication from the ventricular pacing device and being configured to:
      detect ventricular activation events; and
      deliver pacing pulses to the atrium, each pacing pulse of the pacing pulses being timed based on when respective ventricular activation events are detected by the atrial pacing device.

2. The system of claim 1, wherein the ventricular activation event arises due to one of an intrinsic ventricular depolarization or a paced ventricular event.

3. The system of claim 1, wherein the atrial pacing device is operable without a communication link between the atrial pacing device and the ventricular pacing device.

4. A system comprising:
a ventricular pacing device configured for implantation within a ventricle of a heart, the ventricular pacing device configured to sense intrinsic ventricular depolarizations and one of:
  inhibit delivery of pacing pulses responsive to sensed intrinsic ventricular depolarizations; or
  deliver pacing pulses to the ventricle responsive to an absence of sensed intrinsic ventricular depolarizations; and
an atrial pacing device configured for implantation within an atrium of the heart, the atrial pacing device being operable without receiving communication from the ventricular pacing device and being configured to:
  detect ventricular activation events; and
  deliver pacing pulses to the atrium, each pacing pulse of the pacing pulses being timed based on when respective ventricular activation events are detected by the atrial pacing device;
wherein the atrial pacing device is configured to deliver pacing pulses at an atrial pacing rate, and wherein the ventricular pacing device is configured to deliver pacing pulses at a ventricular pacing rate that is less than the atrial pacing rate.

5. The system of claim 4, wherein the ventricular pacing device is configured to detect intrinsic ventricular depolarizations and inhibit the delivery of a pacing pulse to the ventricle upon detection of an intrinsic ventricular depolarization, wherein the ventricular pacing rate is set such that the ventricular pacing device delivers pacing pulses to the ventricle when atrioventricular (AV) block in the heart prevents intrinsic ventricular depolarizations being precipitated by atrial depolarizations.

6. A system comprising:
a ventricular pacing device configured for implantation within a ventricle of a heart, the ventricular pacing device configured to sense intrinsic ventricular depolarizations and one of:
  inhibit delivery of pacing pulses responsive to sensed intrinsic ventricular depolarizations; or
  deliver pacing pulses to the ventricle responsive to an absence of sensed intrinsic ventricular depolarizations; and
an atrial pacing device configured for implantation within an atrium of the heart, the atrial pacing device being operable without receiving communication from the ventricular pacing device and being configured to:
  detect ventricular activation events; and
  deliver pacing pulses to the atrium, each pacing pulse of the pacing pulses being timed based on when respective ventricular activation events are detected by the atrial pacing device;
wherein the atrial pacing device is configured to:
determine a length of an interval between a ventricular activation event of the ventricular activation events and a respective previous atrial event;
schedule a time at which to deliver a pacing pulse of the pacing pulses to the atrium based on the length of the interval; and
control the delivery of the pacing pulse of the pacing pulses at the scheduled time.

7. The system of claim 6, wherein the atrial pacing device is configured to:
sense ventricular electrical activity; and
detect the ventricular activation events by detecting the ventricular electrical activity.

8. The system of claim 7, wherein the ventricular electrical activity comprises a far-field R-wave.

9. The system of claim 6, wherein the atrial pacing device includes a sensor that generates signals that indicate mechanical cardiac characteristics, and wherein the atrial pacing device is configured to detect contraction of the ventricle based on the generated signals.

10. A method comprising:
sensing intrinsic ventricular depolarizations of a ventricle of a heart using a ventricular pacing device configured for implantation within the ventricle;
delivering pacing pulses to the ventricle of the heart using the ventricular pacing device responsive to an absence of the sensed intrinsic ventricular depolarizations;
detecting ventricular activation events using an atrial pacing device that is operable without receiving communication from the ventricular pacing device and configured for implantation entirely within an atrium of the heart; and
delivering, by the atrial pacing device, pacing pulses to the atrium, each pacing pulse of the pacing pulses being timed based on when respective ventricular activation events are detected by the atrial pacing device.

11. The method of claim 10, wherein the ventricular activation events arise due to one of respective intrinsic ventricular depolarizations or respective paced ventricular events.

12. The method of claim 10, wherein the atrial pacing device is operable without a communication link between the atrial pacing device and the ventricular pacing device.

13. A method comprising:
sensing intrinsic ventricular depolarizations of a ventricle of a heart using a ventricular pacing device configured for implantation within the ventricle;
delivering pacing pulses to the ventricle of the heart using the ventricular pacing device;
detecting ventricular activation events using an atrial pacing device that is operable without receiving communication from the ventricular pacing device and configured for implantation within an atrium of the heart;
delivering, by the atrial pacing device, pacing pulses to the atrium, each pacing pulse of the pacing pulses being timed based on when respective ventricular activation events are detected by the atrial pacing device;
delivering pacing pulses at an atrial pacing rate using the atrial pacing device; and
delivering pacing pulses at a ventricular pacing rate that is less than the atrial pacing rate using the ventricular pacing device.

14. The method of claim 13, further comprising inhibiting the delivery of a pacing pulse to the ventricle upon detection of an intrinsic ventricular depolarization, wherein the ventricular pacing rate is set such that pacing pulses are delivered to the ventricle when atrioventricular (AV) block in the heart prevents intrinsic ventricular depolarizations being precipitated by atrial depolarizations.

15. A method comprising:
sensing intrinsic ventricular depolarizations of a ventricle of a heart using a ventricular pacing device configured for implantation within the ventricle;
delivering pacing pulses to the ventricle of the heart using the ventricular pacing device;
detecting ventricular activation events using an atrial pacing device that is operable without receiving communication from the ventricular pacing device and configured for implantation within an atrium of the heart;

delivering, by the atrial pacing device, pacing pulses to the atrium, each pacing pulse of the pacing pulses being timed based on when the ventricular activation events are detected by the atrial pacing device;

delivering pacing pulses at an atrial pacing rate using the atrial pacing device;

delivering pacing pulses at a ventricular pacing rate that is less than the atrial pacing rate using the ventricular pacing device;

determining a length of an interval between a ventricular activation event of the ventricular activation events and a respective previous atrial event;

scheduling a time at which to deliver a pacing pulse of the pacing pulses to the atrium based on the length of the interval; and controlling the delivery of the pacing pulse of the pacing pulses at the scheduled time.

16. The method of claim 15, further comprising:
sensing ventricular electrical activity; and
detecting the ventricular activation events by detecting the ventricular electrical activity.

17. The method of claim 16, wherein the ventricular electrical activity comprises a far-field R-wave.

18. The method of claim 15, further comprising:
generating signals that indicate mechanical cardiac characteristics; and
detecting contraction of the ventricle based on the generated signals.

19. A system comprising:
a first pacing device configured for implantation entirely within a first chamber of a heart, the first pacing device configured to sense intrinsic depolarizations of the first chamber of the heart and one of:
  inhibit delivery of pacing pulses responsive to sensed intrinsic depolarizations of the heart; or
  deliver pacing pulses to the heart responsive to an absence of sensed intrinsic depolarizations of the heart; and
a second pacing device configured for implantation entirely within a second chamber of the heart, the second pacing device being operable without a communication link between the first pacing device and the second pacing device, wherein the second pacing device is configured to deliver pacing pulses to the heart timed based on when respective events, from a chamber of the heart different from the second chamber, are detected by the second pacing device.

20. The system of claim 19, wherein the second pacing device is configured to deliver pacing pulses at a second pacing rate, and wherein the first pacing device is configured to deliver pacing pulses at a first pacing rate that is less than the second pacing rate.

21. The system of claim 20, wherein the first pacing device is configured to detect intrinsic ventricular depolarizations and inhibit the delivery of a pacing pulse to the ventricle upon detection of an intrinsic ventricular depolarization, wherein the first pacing rate is set such that the first pacing device delivers pacing pulses to the ventricle when atrioventricular (AV) block in the heart prevents intrinsic ventricular depolarizations being precipitated by atrial depolarizations.

22. The system of claim 19, wherein the second pacing device is configured to:
determine a length of an interval between an event of the respective events detected from the chamber different from the second chamber of the heart and a respective previous event detected from the second chamber of the heart;
schedule a time at which to deliver a pacing pulse to the second chamber based on the length of the interval; and
control the delivery of the pacing pulse of the pacing pulses at the scheduled time.

23. The system of claim 22, wherein the second pacing device is configured to:
sense ventricular electrical activity; and
detect the respective events from the chamber different from the second chamber by detecting the ventricular electrical activity.

24. The system of claim 23, wherein the ventricular electrical activity comprises a far-field R-wave.

25. The system of claim 19, wherein:
the first chamber of the heart comprises a ventricle of the heart,
the second chamber of the heart comprises an atrium of the heart, the first pacing device is a ventricular pacing device configured for implantation within the ventricle of the heart, and the second pacing device is configured for implantation within the atrium of the heart.

* * * * *